United States Patent [19]

Dean et al.

[11] Patent Number: 5,240,923
[45] Date of Patent: Aug. 31, 1993

[54] SULFONAMIDES USEFUL AS CARBONIC ANHYDRASE INHIBITORS

[75] Inventors: Thomas R. Dean, Weatherford; Hwang-Hsing Chen; Jesse A. May, both of Fort Worth, all of Tex.

[73] Assignee: Alcon Laboratories, Inc., Fort Worth, Tex.

[21] Appl. No.: 775,313

[22] Filed: Oct. 9, 1991

Related U.S. Application Data

[63] Continuation-in-part of Ser. No. 618,765, Nov. 27, 1990, Pat. No. 5,153,192, which is a continuation-in-part of Ser. No. 506,780, Apr. 9, 1990, abandoned.

[51] Int. Cl.$^5$ .................. C07D 513/04; A61K 31/54
[52] U.S. Cl. .................. 514/226.5; 544/48; 540/552; 548/207; 548/209; 548/212; 514/373; 514/211
[58] Field of Search .............. 544/48; 548/207, 209, 548/212; 540/552; 514/226.5, 373, 211

[56] References Cited

U.S. PATENT DOCUMENTS

| | | | |
|---|---|---|---|
| 4,731,368 | 3/1988 | Hoffman, Jr. et al. | 514/301 |
| 4,746,745 | 5/1988 | Maren | 548/139 |
| 4,797,413 | 1/1989 | Baldwin et al. | 514/432 |
| 4,847,289 | 7/1989 | Baldwin et al. | 514/445 |

FOREIGN PATENT DOCUMENTS 1096916 1/1961 Fed. Rep. of Germany .
1516024 6/1978 United Kingdom .

OTHER PUBLICATIONS

"The Reactions of Some Thiophene Sulfonyl Derivatives," Cremyln et al., *Phosphorus and Sulfur*, vol. 10, pp. 111–119, 1981.

"Studien in der Thiophenreihe. XXIV.$^2$ Uber Nitrothiophene and Thiophensulfochloride," Steinkopf et al., *Justus Liebigs Analen Der Chemie*, vol. 501, pp. 174–186, 1933.

"Heterocyclic Disulphonamides and Their Diuretic Properties," deStevens et al., *Journal of Medicinal and Pharmaceutical Chemistry*, vol. 1(6), pp. 565–576, 1959.

*Primary Examiner*—John M. Ford
*Attorney, Agent, or Firm*—James A. Arno; Sally S. Yeager

[57] ABSTRACT

Sulfonamides and pharmaceutical compositions containing the compounds useful in controlling intraocular pressure are disclosed. Methods for controlling intraocular pressure through administration of the compositions are also disclosed.

14 Claims, No Drawings

SULFONAMIDES USEFUL AS CARBONIC ANHYDRASE INHIBITORS

This application is a continuation-in-part of U.S. patent application Ser. No. 618,765, filed Nov. 27, 1990, now U.S. Pat. No. 5,153,192 which is a continuation-in-part of U.S. patent application Ser. No. 506,780, filed Apr. 9, 1990, now abandoned.

FIELD OF THE INVENTION

The present invention relates to new sulfonamides useful in lowering and controlling intraocular pressure.

BACKGROUND OF THE INVENTION

Glaucoma is a disease of the eye which is characterized by a progressive loss of visual field due to irreversible damage to the optic nerve to the point where if untreated can result in total blindness. This loss of visual field, in one form of primary open angle glaucoma, or POAG, is associated with a sustained increase in the intraocular pressure (IOP) of the diseased eye. Moreover, elevated intraocular pressure without visual field loss is thought to be indicative of the early stages of this form of POAG.

There are a number of therapies that target reducing the elevated IOP associated with this form of POAG. The most common feature the topical administration of a beta adrenergic antagonist or a muscarinic agonist. These treatments while effective in lowering IOP can also produce significant undesirable side effects.

Another less common treatment for this form of POAG is the systemic administration of carbonic anhydrase inhibitors. However, these drugs also can bring about unwanted side effects, such as nausea, dyspepsia, fatigue, and metabolic acidosis.

U.S. Pat. Nos. 4,797,413, 4,847,289 and 4,731,368 disclose topically dosed thiophene sulfonamides which lower IOP by inhibiting carbonic anhydrase.

Thiophene bis-sulfonamides, which are carbonic anhydrase inhibitors useful for treating conditions attributable to a restriction of blood flow to the brain, including atherosclerosis, occlusion of blood vessels in the brain, stroke and other cerebra vascular diseases, are disclosed in the British Patent No. 1,516,024. Similar compounds are also disclosed in *Justus Liebigs Annalen der Chemie*, 1933, 501, 174–188 and in *Phosphorus Sulfur*, 1981, 10(1), 111–119.

Other thiophene bis-sulfonamides, which are carbonic anhydrase inhibitors useful as diuretics, are disclosed in the German Patent No. 1,096,916 and *Journal of Medicinal and Pharmaceutical Chemistry*, 1959, 1(6), 565–576.

The compounds of the present invention are new sulfonamides which are carbonic anhydrase inhibitors useful for lowering IOP without producing significant systemic side effects when delivered topically to the eye.

SUMMARY OF THE INVENTION

The present invention is directed to new sulfonamides which can be used to lower and control IOP. The compounds are formulated in pharmaceutical compositions for delivery.

The invention is also directed to methods for lowering and controlling IOP by the administration of the compositions comprising the sulfonamides of the present invention. The compositions can be administered systemically and/or topically to the eye.

DETAILED DESCRIPTION OF THE INVENTION

The sulfonamides of the present invention have the following structure.

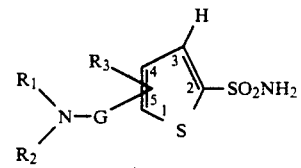

[1]

or a pharmaceutically acceptable salt thereof wherein:

$R_1$ is H; $C_{1-4}$ alkyl; $C_{2-4}$ alkyl substituted optionally with OH, halogen, $C_{1-4}$ alkoxy or $C(=O)R_7$.

$R_2$ is H; $C_{1-8}$ alkyl; $C_{2-8}$ alkyl substituted with OH, $NR_5R_6$, halogen, $C_{1-4}$ alkoxy, $C_{2-4}$ alkoxy $C_{1-4}$ alkoxy, $OC(=O)R_7$, or $C(=O)R_7$; $C_{3-7}$ alkenyl unsubstituted or substituted optionally with OH, $NR_5R_6$, or $C_{1-4}$ alkoxy; $C_{3-7}$ alkynyl unsubstituted or substituted optionally with OH, $NR_5R_6$, or $C_{1-4}$ alkoxy; $C_{1-3}$ alkyl substituted with phenyl or a heteroaromatic group either of which can be unsubstituted or substituted optionally with OH, $(CH_2)_n NR_5R_6$, halogen, $C_{1-4}$ alkoxy, $C_{1-4}$ haloalkoxy, $C(=O)R_7$, $S(=O)_m R_8$ or $SO_2NR_5R_6$, wherein m is 0–2 and n is 0–2; $C_{2-4}$ alkoxy substituted optionally with $NR_5R_6$, halogen, $C_{1-4}$ alkoxy, or $C(=O)R_7$; phenyl or a heteroaromatic group either of which can be unsubstituted or substituted optionally with OH, $(CH_2)_n NR_5R_6$ halogen, $C_{1-4}$ alkoxy, $C_{1-4}$ haloalkoxy, $C(=O)R_7$, $S(=O)_m R_8$ or $SO_2NR_5R_6$, wherein m is 0–2 and n is 0–2; provided that $R_1$ and $R_2$ cannot both be H; or $R_1$ and $R_2$ can be joined to form a saturated ring of 5 or 6 atoms selected from O, S, C so or N, such as, pyrrolidine, oxazolidine, thiomorpholine, thiomorpholine 1,1 dioxide, morpholine, piperazine, thiazolidine 1,1 dioxide, or tetrahydrooxazine, which can be unsubstituted or substituted optionally on carbon with OH, $NR_5R_6$, halogen, $C_{1-4}$ alkoxy, $C(=O)R_7$, $C_{1-6}$ alkyl, $C_{1-6}$ alkyl substituted optionally with OH, $NR_5R_6$, halogen, $C_{1-4}$ alkoxy, $C(=O)R_7$ or on nitrogen with $NR_5R_6$, $C_{1-4}$ alkoxy, $C(=O)R_7$, $C_{1-6}$ alkyl or $C_{2-6}$ alkyl substituted optionally with OH, $NR_5R_6$, halogen, $C_{1-4}$ alkoxy or $C(=O)R_7$.

$R_3$ is H; halogen; $C_{1-4}$ alkyl; $C_{1-8}$ alkoxy; $C_{1-8}$ alkylthiol; $C_{1-8}$ alkoxy substituted optionally with OH, $NR_5R_6$, halogen, $C_{1-4}$ alkoxy or $C(=O)R_7$; $C_{1-4}$ alkyl substituted optionally with $R_4$; or $R_1$ and $R_3$ can be joined together with carbon atoms to form a ring of from 5 to 7 members in which said carbon atoms can be unsubstituted or substituted optionally with $R_4$.

$R_4$ is OH; $C_{1-4}$ alkyl unsubstituted or substituted optionally with OH, $NR_5R_6$, halogen, $C_{1-4}$ alkoxy or $C(=O)R_7$; $C_{1-4}$ alkoxy; $C_{2-4}$ alkoxy substituted optionally with OH, $NR_5R_6$, halogen, $C_{1-4}$ alkoxy or $C(=O)R_7$; $NR_5R_6$; phenyl or a heteroaromatic group either of which can be unsubstituted or substituted optionally with OH, $(CH_2)_n NR_5R_6$, halogen, $C_{1-4}$ alkoxy, $C_{1-4}$ haloalkoxy, $C(=O)R_7$, $S(=O)_m R_8$ or $SO_2NR_5R_6$, wherein m is 0–2 and n is 0–2;

Provided that when G is SO$_2$ and R$_3$ is in the 4 position and is H or halogen then R$_1$ and R$_2$ are not H, C$_{1-6}$ alkyl substituted optionally with OH, C$_{1-6}$ alkoxy, C$_{2-6}$ alkoxycarbonyl, C$_{2-6}$ alkenyl, phenyl, phenoxy, pyridyl, tetrahydrofuryl, C$_{2-6}$ alkanoyl, C$_{2-6}$ alkenyl, nor are they joined to form a 5, 6 or 7 member ring, saturated or unsaturated, comprised of atoms selected optionally from C, O, S, N in which said nitrogen, when saturated, is substituted optionally with H or C$_{1-6}$ alkyl or in which said carbon is substituted optionally with C$_{1-6}$ alkyl, C$_{1-6}$ alkoxy or OH; and when R$_3$ is in the 5 position and is H, Cl, Br, or C$_{1-3}$ alkyl then neither R$_1$ nor R$_2$ can be H or C$_{1-4}$ alkyl; and when G is C(=O) and in the 5- position and R$_3$ is H, then R$_1$ and R$_2$ cannot both be CH$_3$;

R$_5$ & R$_6$ are the same or different and are H; C$_{1-4}$ alkyl; C$_{2-4}$ alkyl substituted optionally with OH, halogen, C$_{1-4}$ alkoxy or C(=O)R$_7$; C$_{1-4}$ alkoxy; C$_{2-4}$ alkoxy substituted optionally with OH, halogen, C$_{1-4}$ alkoxy or C(=O)R$_7$; C$_{3-7}$ alkenyl unsubstituted or substituted optionally with OH, NR$_5$R$_6$, or C$_{1-4}$ alkoxy; C$_{3-7}$ alkynyl unsubstituted or substituted optionally with OH, NR$_5$R$_6$, or C$_{1-4}$ alkoxy; C$_{1-2}$alkyl C$_{3-5}$-cycloalkyl; C(=O)R$_7$ or R$_5$ and R$_6$ can be joined to form a ring of 5 or 6 atoms selected from O, S, C or N, such as, pyrrolidine, oxazolidine, thiomorpholine, thiomorpholine 1,1 dioxide, morpholine, piperazine, thiazolidine 1,1-dioxide, or tetrahydrooxazine, which can be unsubstituted or substituted optionally on carbon with OH, (=O), halogen, C$_{1-4}$ alkoxy, C(=O)R$_7$, C$_{1-6}$ alkyl, C$_{1-6}$ alkyl substituted optionally with OH, halogen, C$_{1-4}$ alkoxy, C(=O)R$_7$ oron nitrogen with C$_{1-4}$ alkoxy, C(=O)R$_7$, S(=O)$_m$R$_8$, C$_{1-6}$ alkyl or C$_{2-6}$ alkyl substituted optionally with OH, halogen, C$_{1-4}$ alkoxy, C(=O)R$_7$ or on sulfur by (=O)$_m$, wherein m is 0-2.

R$_7$ is C$_{1-8}$ alkyl; C$_{1-8}$ alkyl substituted optionally with OH, NR$_5$R$_6$, halogen, C$_{1-4}$ alkoxy or C(=O)R$_9$; C$_{1-4}$ alkoxy; C$_{2-4}$ alkoxy substituted optionally with OH, NR$_5$R$_6$, halogen or C$_{1-4}$ alkoxy; NR$_5$R$_6$; or phenyl or a heteroaromatic group either of which can be unsubstituted or substituted optionally with OH, halogen, C$_{1-3}$ alkyl, C$_{1-3}$ haloalkoxy, (CH$_2$)n NR$_5$R$_6$, S(=O)mR$_8$ or SO$_2$NR$_5$R$_6$, wherein n is 0 or 1 and m is 0-2.

R$_8$ is C$_{1-4}$ alkyl; C$_{2-4}$ alkyl substituted optionally with OH, NR$_5$R$_6$, halogen, C$_{1-4}$ alkoxy or C(=O)R$_7$.

R$_9$ C$_{1-4}$ alkyl; C$_{1-4}$ alkoxy; amino, C$_{1-3}$ alkylamino, or di-C$_{1-3}$ alkylamino and G is C(=O) or SO$_2$.

In the above definitions, the total number of carbon atoms in a substituent group is indicated by the C$_{i-j}$ prefix where i and j are numbers from 1 to 8 for example. This C$_{i-j}$ definition includes both the straight and branched chain isomers. For example, C$_{1-4}$ alkyl would designate methyl through the butyl isomers; and C$_{1-4}$ alkoxy would designate methoxy through the butoxy isomers.

The term "halogen," either alone or in compound words such as "haloalkyl," means fluorine, chlorine, bromine or iodine. Further, when used in compound words such as "haloalkyl," said alkyl may be partially or fully substituted with halogen atoms, which may be the same or different.

The term heteroaromatic means a monocyclic ring system of 5 or 6 atoms comprised of C, N, O and or S such as furan, thiophene, pyrrole, pyrazole, imidazole, triazole, tetrazole, oxazole, isoxazole, isothiazole, thiazole, thiadiazole, pyridine, pyrimidine, pyridazine, and pyrazine.

Structure [I] includes isomers, wherein R$_3$ and GNR$_1$R$_2$ are attached to the 4 and 5 position respectively or R$_3$ is attached to the 5 position and GNR$_1$R$_2$ is attached to the 4 position. Many of the novel compounds of Structure [I] possess one or more chiral centers and this invention includes all enantiomers, diastereomers and mixtures thereof.

SYNTHESIS

Compounds of the present invention can be prepared using a variety of procedures, a number of which are described below in equations 1 through 7.

Many of the novel compounds of Structure [I] can be prepared from N-t-Bu thiophene-2-sulfonamides with R$_3$ substituents according to the scheme shown in equation 1.

In general, N-t-Bu thiophene-2-sulfonamides can be metallated in the 5-position at low temperatures using a strong organometallic base such as n-butyllithium and condensed with sulfur dioxide gas to produce intermediate sulfinate salts (equation 1a). These intermediates can be readily oxidized to the corresponding sulfonyl chloride which in turn can be aminated with primary or secondary amines, bearing the requisite R$_1$ and R$_2$ substituents, to furnish the novel compounds of Structure [I] (equation 1b).

In many cases it is more advantageous to prepare initially simplified primary or secondary sulfonamides via the above sequence and then append the more complex R$_1$ and/or R$_2$ substituents using standard alkylation reactions (equation 1c). This sequence can furnish directly the novel compounds of Structure [1] or the R$_1$, R$_2$ and R$_3$ substituents can be modified to furnish the cyclic and/or acyclic novel compounds of Structure [1] using methods known to one skilled in the art. Primary sulfonamides can be prepared from the corresponding sulfonyl chloride by amination with ammonia or directly from sulfinate salts using hydroxylamine-O-sulfonic acid (equation 1d).

Equation 1

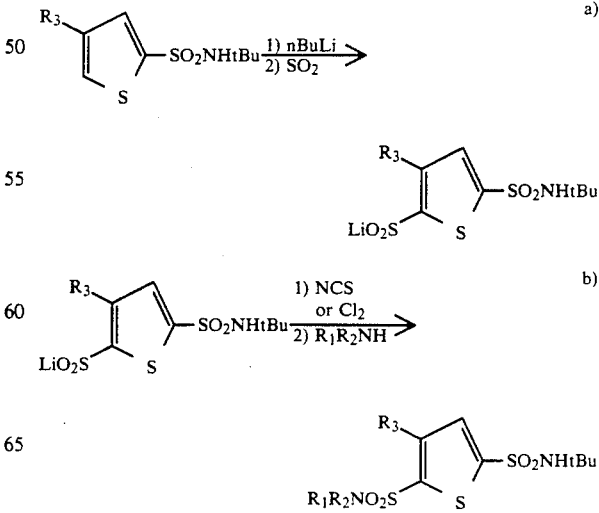

-continued
Equation 1

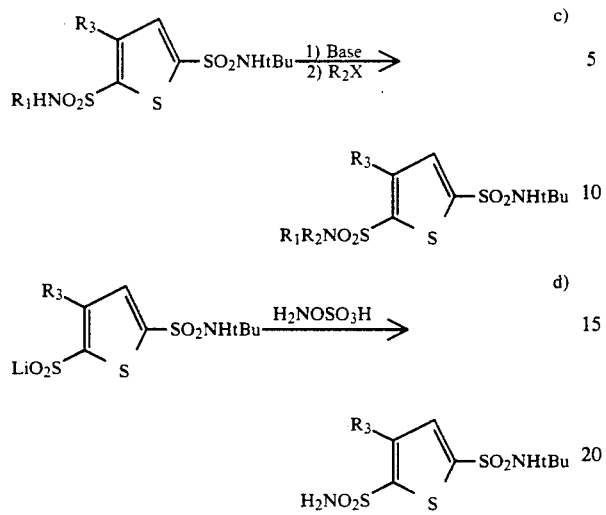

Many of the compounds of Structure [I] can be prepared using the procedures shown below in equation 2.

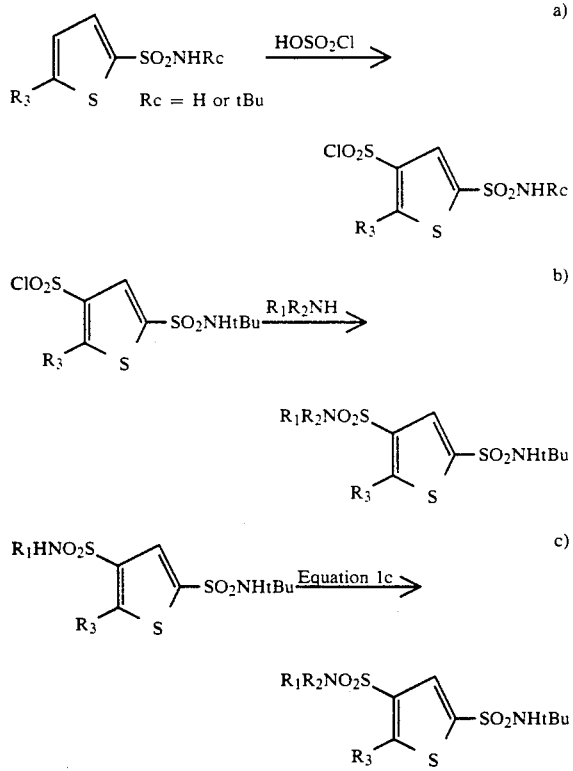

Chlorosulfination of thiophene 2-sulfonamides produce the 4-sulfonyl chlorides (equation 2a). These intermediate sulfonyl chlorides can be converted to the novel compounds of Structure [I] using the procedures (equations 2b and c) analogous to those described for equation 1.

Many of the novel compounds of Structure [I] can be prepared according the schemes shown below in equations 3 and 4.

Equation 3

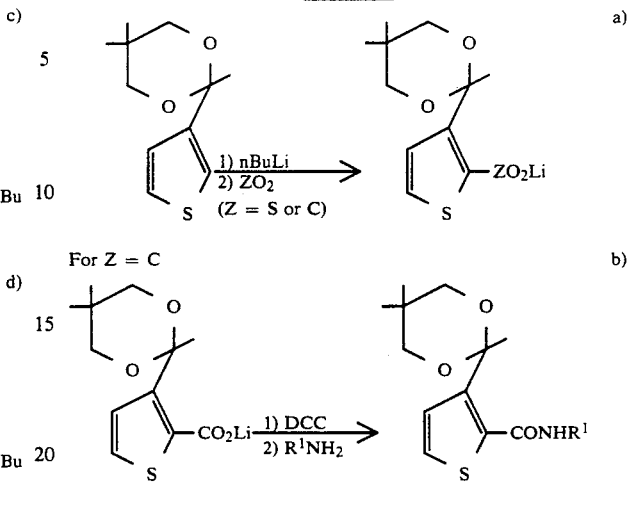

Ketals (equation 3a) can be metallated in the 2 position with a strong organometallic base such as n-butyllithium and condensed with $SO_2$ or $CO_2$ gas to furnish intermediate sulfinic acid or carboxylic acid salts in a way similar to that described in equation 1a. The sulfinic acid salts can be transformed into 2-sulfonamides derivatives via the two procedures outlined above in equations 1b and c. The carboxylic acid salts can be converted in a similar way as shown in equation 3b. The conversion of these acyclic sulfonamides and carboxamides into the desired cyclic compounds of Structure [I] can be accomplished using a variety of procedures well known in the art. Selected sequences are outlined in equations 4a, b and c.

Equation 4

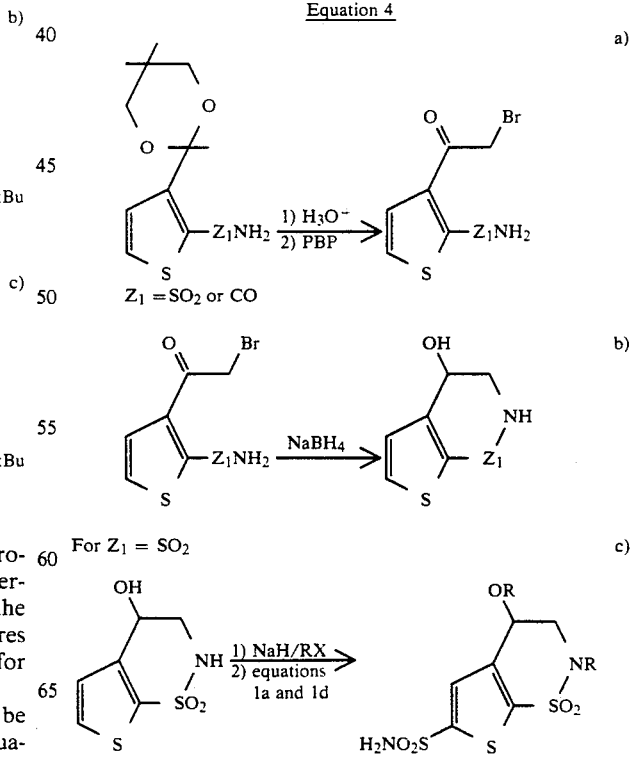

Equation 4 -continued

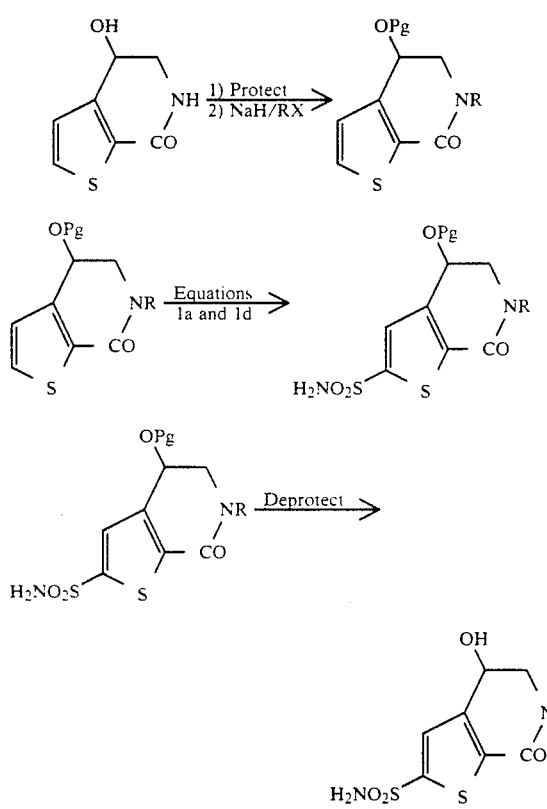

Equation 5

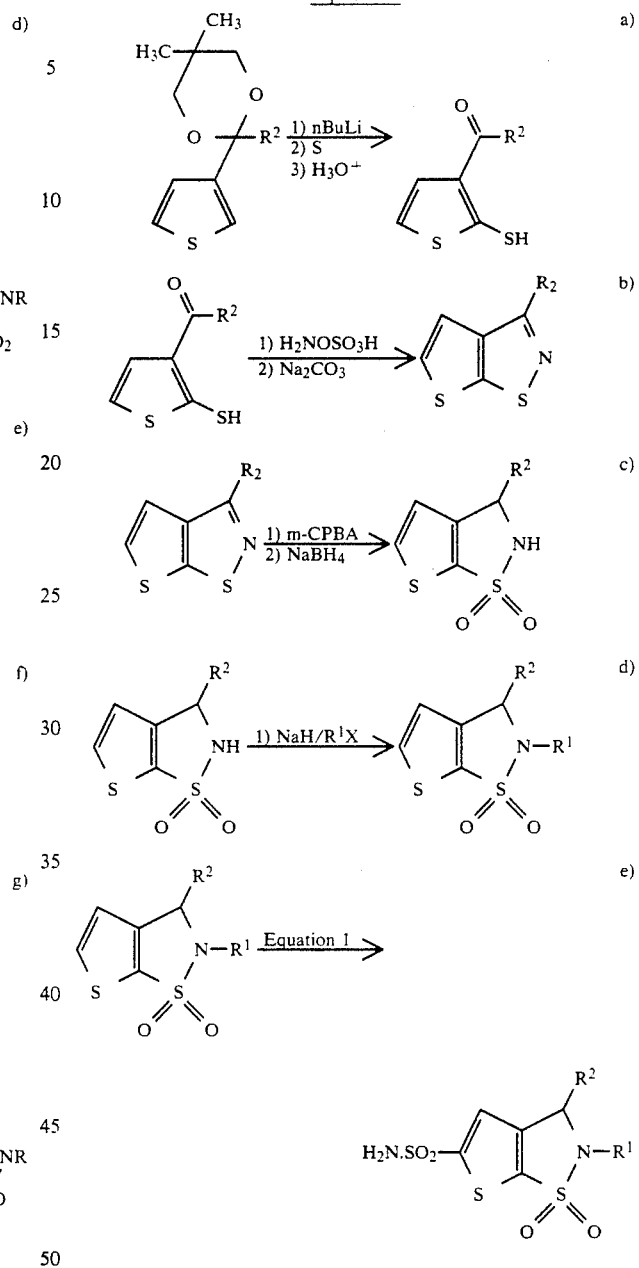

Certain cyclic compounds of Structure [I], such as the 2,3-dihydrothienoisothiazoles, can be obtained through the modification of an existing cyclic compound (equation 5). The metallated ketals of equation 3 can be readily converted to the desired intermediate mercaptoketones as shown in equation 5a, and the oxime O-esters of such compounds can be cyclized according to equation 5b. Oxidation and subsequent reduction of the thienoisothiazole by procedures well known in the art provides the intermediate cyclic sulfonamides shown in equation 5c. These cyclic sulfonamides can be substituted on nitrogen utilizing standard alkylation conditions such as demonstrated by equation 5d. Incorporation of the primary sulfonamide into position five of these examples of Structure [I] can be accomplished under the basic conditions demonstrated by equations 1a–d.

Yet other cyclic compounds of Structure [I], such as tetrahydrothienothiazepines, can be prepared from substituted thiophenesulfonamides according to equation 6. Thiophene acetals can be metallated in the two position with strong metallic bases in a manner similar to that described in equation 3a for thiophene ketals. These intermediates can be further converted to the thiophene-2-sulfonamides desired for equation 6a in a manner similar to that described for thiophene ketals by equations 3a and 1d. Thiophene acetals can be readily converted to the corresponding aldehydes by acid hydrolysis, and reaction of these aldehydes with an olefinic Grignard reagent can provide the olefin intermediates of equation 6a. The allylic alcohols from equation 6a can be oxidized to intermediate ketones by a variety of procedures well known to the art, and these ketones can be cyclized upon treatment under basic conditions, such as sodium carbonate, to the cyclic sulfonamides (equation 6b). The requisite $R_1$ group can be appended by using standard alkylation reactions (equation 6c) and these intermediates can be reduced to the requisite alcohols with a suitable reagent, such as sodium borohydride. The alcohols can be transformed to amines by initial conversion to an alkyl or aryl sulfonic acid ester, and subsequent treatment of this intermediate with the desired primary or secondary amine (equation 6d). Introduction of the primary sulfonamide functionality into the tetrahydrothienothiazepines can be accomplished by procedures similar to those already described in equations 1a, 1b, and 1d (equation 6e).

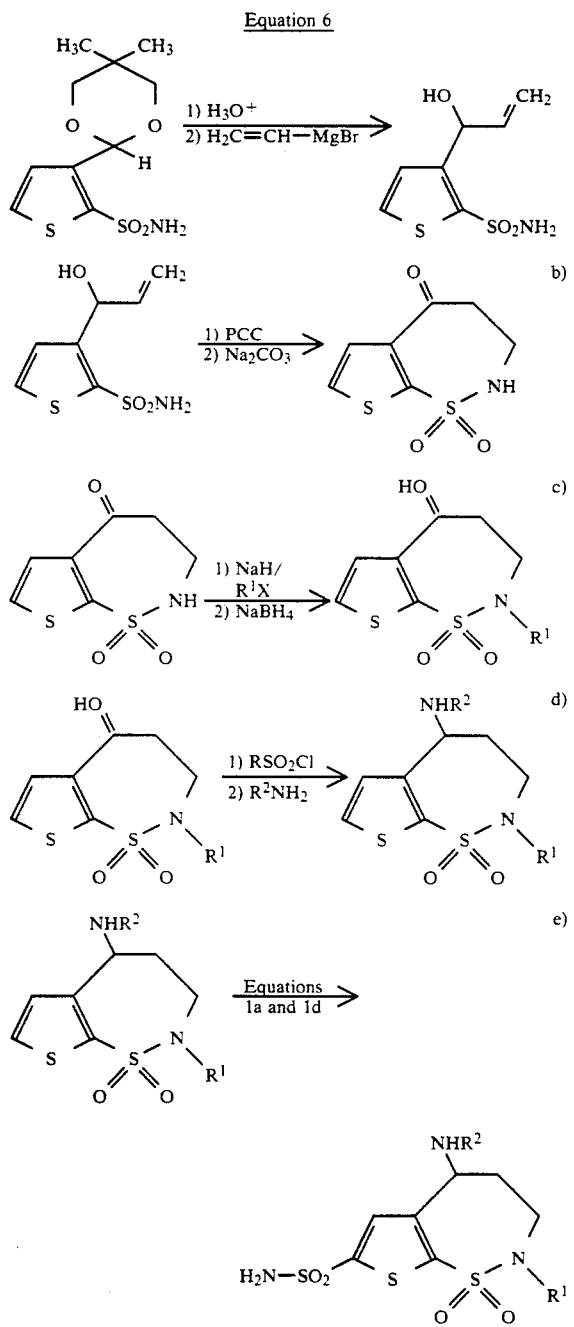

Thienothiazines isomeric to those described in equation 4 can be prepared using a similar route starting from 2,3-dichlorothiophene as shown in equation 7. Chlorosulfination of this starting material followed by amination using methods similar to those described in equation 2 will provide the desired 3-sulfonamide (equation 7a). Subsequent treatment of this intermediate with n-butyllithium at low temperature followed by quenching with a will give rise to the methylketone derivative (equation 7b). This key intermediate can then be converted into the desired novel compounds of Structure [I] using substantially the same general methods described in equation 4.

The compounds of Structure [I] can be incorporated into various types of ophthalmic formulations for delivery to the eye. These compounds may be combined with ophthalmologically acceptable preservatives, surfactants, viscosity enhancers, penetration enhancers, buffers, sodium chloride and water to form an aqueous, sterile ophthalmic suspension or solution. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940 or the like according to the published formulations for analogous ophthalmic preparations; preservatives and tonicity agents can be incorporated. Ophthalmic solution formulations may be prepared by dissolving the active ingredient in a physiologically acceptable isotonic aqueous buffer. Further, the ophthalmic solution may include an ophthalmologically acceptable surfactant to assist in dissolving the active ingredient. Furthermore, the ophthalmic solution may contain a thickener such as hydroxymethylcellulose, hydroxyethylcellulose, hydroxypropylmethylcellulose, methylcellulose, polyvinylpyrrolidone, or the like to improve the retention of the medicament in the conjunctival sac.

The compounds are preferably formulated as topical ophthalmic solutions, with pH of about 4.5 to 7.5. The compounds will normally be contained in these formulations in an amount of 0.1% to 10% by weight, but preferably in an amount of 0.25% to 5.0% by weight. Thus, for topical presentation 1 to 3 drops of these formulations would be delivered to the surface of the eye 1 to 4 times a day according to the routine discretion of a skilled clinician.

The following examples, which are in no way limiting, illustrate the preparation of selected examples of the novel compounds of Structure [I]. The compounds set forth in Examples 17, 18, and 25 represent the preferred thiophene sulfonamides of this invention. The compound represented in Example 25 is most preferred.

EXAMPLE 1

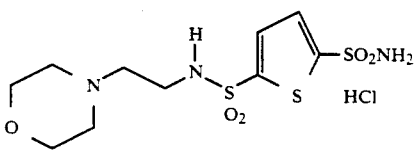

N-[2-(4-morpholinyl)ethyl]-2,5-thiophenedisulfonamide hydrochloride

Step A: N-(1,1-Dimethylethyl)-2-thiophenesulfonamide

To a solution of t-butylamine (8.35 g, 0.114 mol) in dry tetrahydrofuran (THF) (20 mL) cooled to 0° C. was added dropwise 2-thiophenesulfonyl chloride (5.0 g, 27.4 mmol). After the addition was completed, the reaction mixture was warmed to ambient temperature and stirred overnight. The mixture was extracted with ethyl acetate (3×80 mL) and the combined extracts were washed with water, dried over molecular sieves and concentrated. The residue was chromatographed on (silica, eluting with 25% ethyl acetate-hexane) to yield 5.62 g (94%) of solid: mp 80°–82° C.

Step B: N-(1,1-Dimethylethyl)-2,5-thiophenedisulfonamide

To a solution of the product from Step A (1.5 g, 6.85 mmol) in THF (10 mL) cooled to −60° C. was added n-butyllithium in hexane (2.5 M, 6.0 mL, 15.1 mmol). The mixture was stirred for 15 min at −60° C. and for 30 min at −10° C. Sulfur dioxide gas was passed through the surface of the mixture for 10 min. The cooling bath was removed and the mixture was stirred for an additional 1 h.

The volatiles were evaporated and the residue was dissolved in water (30 mL) and sodium acetate trihydrate (5.59 g, 41.1 mmol) was added. The mixture was cooled in an ice-water bath and hydroxylamine-O-sulfonic acid (2.71 g, 23.9 mmol) was added. The cooling bath was removed and the mixture was stirred for 2 h. The suspension was extracted with ethyl acetate (3×50 mL) and the combined extracts were washed with 5% sodium bicarbonate solution, brine and dried over molecular sieves. The solvent was evaporated and the residue was chromatographed on (silica, eluting with 40% ethyl acetate-hexane) to yield 1.25 g (61%) of a liquid which solidified on standing: mp 116°–120° C.

Step C: N-(1,1-Dimethylethyl)-N'-[2-(4-morpholinyl)ethyl]-2,5-thiophenedisulfonamide A solution of the product from Step B (1.05 g, 3.52 mmol), sodium hydride (60% dispersion in mineral oil, 310 mg, 7.75 mmol) and 4-(2-chloroethyl)morpholine hydrochloride (0.721 g, 3.88 mmol) in anhydrous dimethylformamide (DMF) (20 mL) was heated at 110° C. for 2.5 h and then stirred at ambient temperature overnight. The reaction mixture was extracted with ethyl acetate (3×100 mL), washed with brine, dried over molecular sieves and concentrated. The residue was chromatographed (silica, elution with 50% ethyl acetate-hexane) to yield 0.32 g (22%) of the desired product.

Step D: N-[2-(4-Morpholinyl)ethyl]-2,5-thiophenedisulfonamide hydrochloride

A solution of the product from Step C (0.31 g, 0.75 mmol) in trifluoroacetic acid (7 mL) was stirred at ambient temperature for 4 h. The trifluoroacetic acid was evaporated and the residue was chromatographed (silica, eluting with methylene chloride-methanol-ammonium hydroxide (10/1/0.1)) to give 230 mg (86%) of a viscous liquid. The liquid was dissolved in ethanol and treated with ethanolic HCl. Evaporation gave a white solid which was recrystallized from ethanol-water to afford colorless crystals (145 mg): mp 219°–220° C.

Analysis calculated for $C_{10}H_{18}ClN_3O_5S_3$: C, 30.65; H, 4.63; N, 10.72 Found: C, 30.54; H, 4.67; N, 10.64.

Example 2

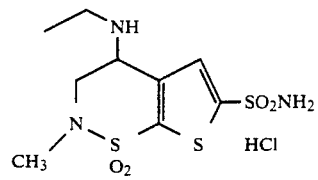

4-Ethylamino-3,4-Dihydro-2-methyl-2H-thieno[3,2-e]-1,2-thiazine-6-sulfonamide 1,1-dioxide hydrochloride

Step A: 3-(2,5,5-Trimethyl-1,3-dioxane-2-yl)-2-thiophenesulfonamide

To a solution of 3-(2,5,5-Trimethyl-1,3-dioxane-2-yl)thiophene (2.5 g, 11.7 mmol) in hexane (30 mL) cooled to 0° C. was added via syringe n-butyllithium in hexane (2.5 M, 10.3 mL, 25.7 mmol) over 5 min. The mixture was stirred at 0° C. for 20 min, the ice bath was removed and the stirring was continued for 30 min. At this time a white precipitate formed. The mixture was cooled to −60° C. and THF (20 mL) was added. Sulfur dioxide was then passed through the surface of the mixture for 30 min. The mixture was warmed to ambient temperature and stirred for an additional 15 min. The volatiles were evaporated and to the residue was added water (50 mL) and sodium acetate trihydrate (9.55 g, 70.2 mmol). The solution was cooled on an ice bath and hydroxylamine-O-sulfonic acid (4.62 g, 40.9 mmol) was added. The mixture was stirred at ambient temperature for 1 h, extracted with ethyl acetate (3×100 mL) and the combined extracts were washed with a sodium bicarbonate solution, brine and dried over molecular sieves. Evaporation to dryness gave a viscous liquid (4.93 g), which was chromatographed (silica, eluting with 33% ethyl acetate-hexane) to give a solid (2.47 g, 72%): mp 200°–202° C.

Step B: 3-Acetyl-2-thiophenesulfonamide

A mixture of the compound from Step A (9.45 g, 32.5 mmol) and 1N HCl (100 mL) in THF (100 mL) was heated at reflux for 1 h. The THF was evaporated and the aqueous solution was made basic by the addition of sodium bicarbonate. The mixture was cooled using an ice bath and the precipatiate was filtered, washed with cold water and dried in vacuo to give 5.83 g (88%) of a solid: mp 193°–196° C.

Step C: 3,4-dihydro-4-hydroxy-2H-thieno[3,2-e]-1,2-thiazine 1,1-dioxide

The product from Step B (5.73 g, 28.0 mmol) was dissolved in hot THF (200 mL). The solution was cooled to 10.C. and pyridinium bromide perbromide (10.73 g, 33.5 mmol) was added. The mixture was allowed to stir at ambient temperature for 1 h. The volatiles were evaporated and the residue was mixed with water. The precipitate was filtered, washed with cold water and dried in vacuo overnight to give 7.77 g of a solid. A portion of this solid (3.49 g, 12.3 mmol) was suspended in ethanol (100 mL) and treated with sodium borohydride (266 mg, 7.04 mmol). The suspension turned clear after 10 min and was heated at reflux for 1 h. The ethanol was evaporated and the residue was extracted with ethyl acetate, washed with brine and evaporated to give the product (1.80 g, 71%): mp 138°–140° C.

Step D:
3,4-Dihydro-4-methoxy-2-methyl-2H-thieno[3,2-e]-1,2-thiazine 1,1-dioxide To a solution of the product from Step C. (2.75 g, 13.4 mmol) in anhydrous DMF (40 mL) cooled to 0° C. was added sodium hydride (60% dispersion in mineral oil, 1.18 g, 29.5 mmol), followed by methyl iodide (2.5 mL, 40.2 mmol). The reaction mixture stirred at ambient temperature for 4 h and was poured onto ice and extracted with ethyl acetate (3×80 mL). Evaporation gave 3.35 g of an orange liquid which was chromatographed (silica, eluting with 50% ethyl acetate-hexane) to give the desired product (2.42 g, 77%): mp 61°–63° C.

Step E:
3,4-Dihydro-4-methoxy-2-methyl-2H-thieno[3,2-e]-1,2-thiazine-6-sulfonamide 1,1-dioxide To a solution of the product from Step D (1.73 g, 7.42 mmol) in THF (15 mL) cooled to −60° C. was added via syringe n-butyllithium in hexane (2.5 M, 3.56 mL, 8.91 mmol) over 5 min. After the addition was completed, the mixture was warmed to 0° C. and stirred for 20 min. The mixture was re-cooled to −60° C. and a stream of sulfur dioxide was passed through the surface of the mixture for 20 min. The mixture was warmed to ambient temperature and the volatiles were evaporated. To the residue was added sodium acetate trihydrate (3.03 g, 22.3 mmol) and water (50 mL) and the mixture was cooled to 0° C. Hydroxylamine-O-sulfonic acid (1.51 g, 13.4 mmol) was added and the mixture was allowed to stir for 30 min. The reaction mixture was extracted with ethyl acetate (3×100 mL), dried over molecular sieves and concentrated to give an orange oil (2.25 g) which solidified on standing. The solid was crystallized from methanol-methylene chloride to give a colorless solid (1.21 g, 52%, first crop): mp 161°–162° C.

Step F:
4-Acetylamino-3,4-dihydro-2-methyl-2H-thieno[3,2-e]-1,2-thiazine-6-sulfonamide 1,1-dioxide To sulfuric acid (5.0 g) cooled to 0° C. was added the product from Step E (1.10 g, 3.81 mmol) dissolved in acetonitrile (35 mL) dropwise over 10 min. The mixture was stirred at ambient temperature for 2.5 days and quenched by the addition of ice and ammonium hydroxide to adjust the pH to 10. The acetonitrile was evaporated and the white precipitate was filtered and dried to give 0.41 g of the desired product. The filtrate was extracted with ethyl acetate. Evaporation to dryness gave an additional 0.33 g of the desired product (total yield 57%). Crystallization from methanol-methylene chloride gave colorless crystals: mp 252°–253° C.

Step G:
4-Ethylamino-3,4-dihydro-2-methyl-2H-thieno[3,2-e]-1,2-thiazine-6-sulfonamide 1,1-dioxide hydrochloride To a suspension of the product from Step F (0.95 g, 2.80 mmol) in anhydrous THF (70 mL) was added slowly a solution of borane-dimethylsulfide complex in THF (2 M, 4.9 mL, 9.8 mmol). The mixture was then heated at gentle reflux and the dimethyl sulfide was distilled out and condensed in a dry-ice cooled receiving flask. The solution was refluxed for an additional 2 h, cooled and concentrated HCl (10 mL) was added. The resulting mixture was heated at reflux for 30 min, cooled and poured into ice and sodium bicarbonate solution. The mixture was extracted with ethyl acetate (3×100 mL) and the combined extracts were concentrated to give a viscous liquid, which was chromatographed (silica, eluting with 5% methanol-methylene chloride) to give a viscous oil (0.67 g, 74%). The oil was dissolved in ethanol (10 mL) and treated with ethanolic HCl. The volatiles were evaporated and the residue was crystallized from acetonitrile-ethanol and then from water: mp 141°–144° C.

Analysis calculated for $C_9H_{16}ClN_3O_4S_3 \cdot H_2O$: C, 28.45; H, 4.78: N, 11.06. Found: C, 28.72; H, 4.54; N, 11.14.

By following the above procedure but using instead ethylbromide or n-propylbromide in Step D the following compounds were prepared:

2-Ethyl-4-ethylamino-3,4-dihydro-2H-thieno[3,2-e]-1,2-thiazine-6-sulfonamide 1,1-dioxide hydrochloride, mp 234° C.

4-Ethylamino-3,4-dihydro-2-propyl-2H-thieno[3,2-e]-1,2-thiazine-6-sulfonamide 1,1-dioxide hydrochloride, mp 260° C.

EXAMPLE 3

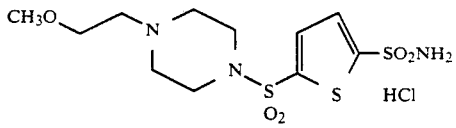

5-[[4-(2-Methoxyethyl)piperazinyl]sulfonyl]-2-thiophenesulfonamide hydrochloride

Step A:
2-[[4-(2-Methoxyethyl)piperazinyl]sulfonyl]thiophene

To a suspension of 1-(2-methoxyethyl)piperazine dihydrochloride (2.61 g, 12.0 mmol) in THF (100 mL) was added triethylamine (10 mL) and the resulting mixture was stirred for 10 min. Then a solution of 2-thiophenesulfonyl chloride (1.98 g, 10.84 mmol) was added in THF (3 mL) over 5 min. The reaction mixture was allowed to stir at room temperature for 1 h, the volatiles were evaporated and the residue was extracted with ethyl acetate (3×100 mL). The combined extracts were washed with a saturated sodium bicarbonate solution (50 mL), brine and dried over molecular sieves. Evaporation to dryness gave a viscous oil (2.09 g, 75%).

Step B:
5-[[4-(2-Methoxyethyl)piperazinyl]sulfonyl]-2-thiophenesulfonamide hydrochloride To a solution of the compound from Step A (2.15 g, 7.41 mmol) in THF (15 mL) cooled to −78° C. was added slowly over 5 min n-butyllithium (2.5 M, 3.86 mL, 9.64 mmol). The mixture was allowed to stir for 40 min when a stream of sulfur dioxide was passed through the surface of the mixture for 30 min. The mixture was warmed to ambient temperature, stirred for an additional 30 min and then evaporated to dryness. The residue was dissolved in water (30 mL) and sodium acetate trihydrate (3.03 g, 22.2 mmol) was added. The mixture was cooled to 0° C. and hydroxylamine-O-sulfonic acid (1.51 g, 13.3 mmol) was added. The mixture was stirred overnight, neutralized with saturated sodium bicarbonate solution and extracted with ethyl acetate (3×80 mL). The combined extracts were washed, dried and evaporated in a manner analogous to Step A to furnish a viscous liquid (2.17 g). This was chromatographed (silica, methylene chloride—methanol—ethyl acetate, 20/1/10)) to give some recovered starting material (1.15 g, 53%) and the desired product (0.82 g, 30%). This product was treated with ethanolic HCl and crystallized from ethanol to furnish white crystals: mp 172°-173° C.

Analysis calculated for $C_{11}H_{20}ClN_3O_5S_3$: C, 32.55; H, 4.97; N, 10.35. Found: C, 32.67; H, 4.92; N, 10.28.

This method can be used to prepary many of the novel compounds of Structure [1] wherein the $R_1$ and $R_2$ substituents are joined to form a ring of 5 to 6 atoms. In many cases the simplified heterocyclic rings used to couple with sulfonyl chlorides, such as that in Step A or those described in equations 1 and 2, are available commercially. Other examples can be prepared using methods known to one skilled in the art. A useful series of references pertinent to this method are "Comprehensive Heterocyclic Chemistry," A. R. Katritzky et al. Volumes 2-6, and references cited therein.

EXAMPLE 4

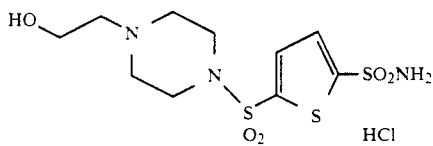

5-[[4-12-Hydroxyethyl)piperazinyl]sulfonyl]-2-thiophenesulfonamide hydrochloride To a solution of 2-[[4-(2-hydroxyethyl)piperazinyl]-sulfonyl]thiophene (2.5 g, 9.0 g mmol) in THF (15 mL) cooled to −78° C. was added slowly over 5 min n-butyllithium (2.5M, 8.5 mL, 20.8 mmol). The mixture was allowed to stir for 40 min at −65° C. and 20 min at −40° C. when a stream of sulfur dioxide was passed through the surface for 30 min. The mixture was warmed to ambient temperature, stirred for 1.5 h then evaporated to dryness. The residue was dissolved in water (30 mL) and sodium acetate trihydrate (6.16 g, 45.3 mmol) was added. The mixture was cooled to 0° C. and hydroxylamine-O-sulfonic acid (3.59 g, 31.7 mmol) was added. The mixture was stirred overnight, neutralized with saturated sodium bicarbonate solution and extracted with ethyl acetate (3×80 mL). The combined extracts were washed, dried and evaporated to furnish a viscous liquid (3.15 9). This was chromatographed (silica, methylene chloride—methanol 70/1) to give some recovered starting material (1.24 g, 50%) and the desired product as a liquid (0.8 g, 25%). The liquid was dissolved in ethanol, filtered and treated with ethanolic HCl. The mixture was filtered and the solid dried to give the desired product (0.54 g): mp 206°-207° C.

Analysis calculated for $C_{10}H_{18}ClN_3O_5S_3$: C,30.65; H, 4.65; N, 10.72 Found: C,30.62; H, 4.64; N, 10.68.

EXAMPLE 5

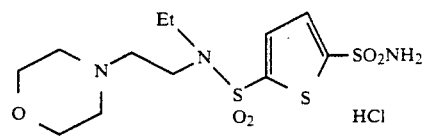

N-Ethyl-N-[2-(4-morpholinyl)ethyl]-2,5-thiophenedisulfonamide hydrochloride

Step A:
N-Ethyl-N-[2-(4-morpholinyl)ethyl]-2-thiophenesulfonamide

To a mixture of sodium hydride (60% dispersion in mineral oil, 0.606 g, 15.1 mmol) in N,N-dimethyl formamide (DMF) (60 mL) cooled to 0° C. was added N-[2-(4-morpholinyl)ethyl]-2-thiophenesulfonamide (3.8 g, 13.8 mmol). The mixture was stirred for 1 h and then allowed to warm to ambient temperature overnight. The mixture was poured onto water, extracted with ethyl acetate, dried and concentrated to furnish a viscous oil (3.81 g). The liquid was dissolved in ethyl acetate and washed with 1 H NaOH, brine, dried and concentrated. This liquid was chromatographed (silica, ethyl acetate) to give the desired product as a liquid (2.95 g, 70%).

Step B:
N-Ethyl-N-[2-(4-morpholinyl)ethyl]-2,5-thiophenedisulfonamide hydrochloride The product from Step A (2.2 g, 7.24 mmol) was treated sequentially with n-butyllithium, sulfurdioxide, hydroxylamine-O-sulfonic acid and ethanolic HCl in much the same way as described in Example 4 to furnish the desired product as a hygroscopic white solid: mp 80°-85° C.

Analysis calculated for $C_{12}H_{22}ClN_3O_5S_3$: C, 34.32; H, 5.28; N, 10.01 Found: C, 34.06; H, 5.20; N, 9.66.

EXAMPLE 6

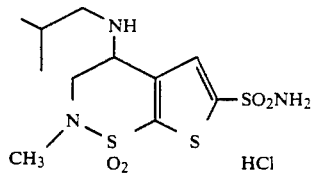

3,4-Dihydro-2-methyl-4-(2-methyl)propylamino-2H-thieno[3,2-e]-1,2-thiazine-6-sulfonamide 1,1-dioxide hydrochloride Step A:
3,4-Dihydro-2-methyl-2H-thieno[3,2-e]-1,2-thiazine-4-ol-1,1-dioxide To a mixture of sodium hydride (60% dispersion in mineral oil, 1.352 g, 33.8 mmol) in DMF (60 mL) was added 2,3-dihydro-4-hydroxy-2H-thieno [2,3-e]-1,2-thiazine 1,1-dioxide (6.30 g, 30.7 mmol), prepared using the procedure described in Example 2. The mixture was cooled (dry ice-acetone bath) and methyl iodide (4.8 9, 33.8 mmol) was added over 5 min. After the addition was complete, the mixture was allowed to warm to ambient temperature and stirred for 2 h. The mixture was then poured onto brine, extracted with ethyl acetate (2×300 mL), dried and concentrated. The residue was chromatographed (silica, first with 50% ethyl acetate/hexane and then with 75% ethyl acetate/hexane) to give the desired product as a liquid (4.9 g, 73%).

Step B:
3,4-Dihydro-2-methyl-4-(2-methyl)propyl-2H-thieno[3,2-e]-1,2-thiazine-4-ol-1,1-dioxide The product from Step B (2.0 g, 9.13 mmol) was dissolved in methylene chloride (50 mL) containing triethylamine (TEA) (1.86 g, 18.3 mmol). The mixture was cooled to −30° C. and solution of tosyl chloride (3.48 g, 18.3 mmol) in methylene chloride (10 mL) was added dropwise over 5 min. The mixture was allowed to warm up to 0° C. gradually for 4.5 h, after which time isobutyl amine (5 mL) was added and the mixture was heated to 50° C. for 4 h and then stirred at ambient temperature overnight. The mixture was poured onto water, extracted with ethyl acetate, dried and concentrated to give the crude product (5.1 g) as a viscous liquid. This liquid was chromatographed (silica, 1/1 ethyl acetate/hexane) to furnish the desired product (1.38 g, 55%) as a liquid.

Step C:
3,4-Dihydro-2-methyl-4-(2-methyl)propylamino-2H-thieno[3,2-e]-1,2-thiazine-6-sulfonamide 1,1-dioxide hydrochloride The product from Step B (1.29 g, 4.71 mmol) was treated sequentially with n-butyllithium, sulfur dioxide, hydroxylamine-0-sulfonic acid and ethanolic HCl in much the same way as described in Example 4 to furnish the desired product as a white solid: mp 141°–144° C.

Analysis calculated for $C_{11}H_{20}ClN_3O_4S_3$—0.5 $H_2O$: C, 33.12; H, 5.31; N, 10.53 Found: C, 33.16; H, 5.14; N, 10.49.

EXAMPLE 7

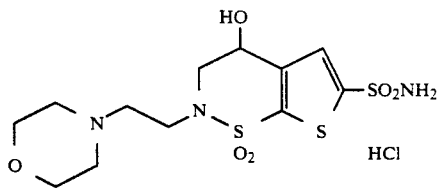

3,4-Dihydro-4-hydroxy-2-12-(4-morpholinyl)ethyl]-2H-thieno[3,2-e]-1,2-thiazine-6-sulfonamlde 1,1-dioxide hydrochloride Step A:
3,4-Dihydro-4-hydroxy-2-[2-(4-morpholinyl)ethyl]-2H-thieno [3,2-e]-1,2-thiazine 1,1-dioxide The selective alkylation of 2,3-dihydro-4-hydroxy-2H-thieno[2,3-e]-1,2-thiazine 1,1-dioxide (3.0 g, 14.6 mmol) with 2-chloroethyl morpholine (5.43 g, 29.2 mmol), using essentially the same procedure as described in Example 6, Step A, gave the desired product (2.25 g, 48%) as a viscous liquid.

Step B:
3,4-Dihydro-4-hydroxy-2-[2-(4-morpholinyl)ethyl]-2H-thieno[3,2-e]-1,2-thiazine-6-sulfonamide 1,1-dioxide hydrochloride The product from Step A (1.84 g, 5.79 mmol) was treated sequentially with n-butyllithium (2.2 equivalents), sulfur dioxide, hydroxylamine-O-sulfonic acid and methanolic HCl in much the same was as described in Example 4 to furnish the desired product as a white solid: mp 118°–125° C.

Analysis calculated for $C_{12}H_{20}ClN_3O_6S_3$: H, 33.21; H, 4.65; N, 9.68. Found: C, 32.81; H, 4.31; N, 9.37.

EXAMPLE 8

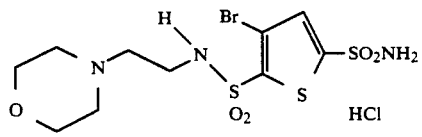

4-Bromo-5-[[2-(4-morpholinyl)ethyl]amino]sulfonyl-2-thiophenesulfonamide hydrochloride Step A:
4-Bromo-5-chlorosulfonyl-2-thiophenesulfonamide To a stirring suspension of 4-bromo-5-(phenylmethyl)thio-2-thiophenesulfonamide (8.5 g, 23.0 mmol) in 1/1 acetic acid/water (70 mL) at 0° C. was passed chlorine gas for 1 h. The excess chlorine was flushed from the reaction mixture with a stream of nitrogen and the resultant solution was poured onto water (20 mL). The mixture was extracted with diethyl ether (3×40 mL) and the combined extracts were washed with water (2×20 mL), dried and concentrated to furnish the desired product (6.0 g, 76%) as a yellow oil.

Step B:
4-Bromo-5-[[2-(4-morpholinyl)ethyl]amino]sulfonyl-2-thiophenesulfonamide hydrochloride The product from Step A (2.3 g, 6.0 mmol) in THF (5 mL) was added dropwise to a cooled solution (0° C.) of triethylamine (1.5 g) and 4-(2-aminoethyl)-morpholine (1.95 g, 15 mmol) in THF (15 mL). The solution was stirred at 0° C. for 1 h and then was warmed to ambient temperature for an additional hour. The reaction mixture was concentrated, the residue was diluted with water and extracted with ethyl acetate (3×50 mL). The combined extracts were washed with brine (10 mL), dried and concentrated to furnish the desired product as a white solid. The material was dissolved in ethanol and treated with ethanolic HCl and the resultant solid was isolated by filtration and dried. The desired product was obtained as a white solid: mp 180°–182° C.

Analysis calculated for $C_{10}H_{17}BrClN_3O_5S_3$: C, 25.80; H, 3.67; N, 8.74 Found: C, 25.51; H, 3.64; N, 8.92.

EXAMPLE 9

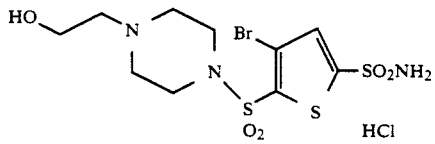

4-Bromo-5-[[4-(2-hydroxyethyl)-piperazinyl]sulfonyl]-2-thiophenesulfonamide hydrochloride A sample of 4-bromo-5-chlorosulfonyl-thiophene-2-sulfonamide (5.2 g, 15.2 mmol) was treated sequentially with 1-(2-hydroxyethyl)-piperazine (4.97 g, 38.0 mmol) and ethanolic HCl in much the same way as described in Example 8, Step B, to -furnish the desired hydrochloride salt. This material was recrystallized from methanol to give a white solid: mp 212° C.

Analysis calculated for $C_{10}H_{17}BrClN_3O_5S_3$—0.25 $H_2O$: C, 25.27; H, 3.71; N, 8.84 Found: C, 25.47; H, 3.51; N, 8.46

EXAMPLE 10

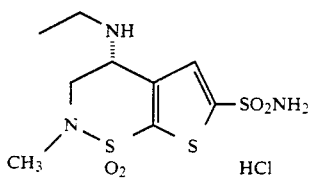

R-(+)-4-Ethylamino-3,4-dihydro-2-methyl-2H-thieno[3,2-e]-1,2-thiazine-6-sulfonamide 1,1-dioxide hydrochloride A hot solution (about 80° C.) of the free base corresponding to Example 2 (10.88 g, 33.5 mmol) in n-propanol (250 mL) was mixed with a hot solution of di-p-toluoyl-D-tartaric acid (3.27 g, 8.47 mmol) in n-proponol (250 mL). Activated carbon (2.0 g) was added and the mixture was kept at greater than 50° C. for 30 min and filtered through a pad of celite. The filtrate was concentrated to about 200 mL and was placed in the freezer overnight. The solid was filtered, washed with cold n-propanol and dried to give the tartrate salt (6.95 g), which was recrystallized four times from hot n-propanol (250, 200, 160 and 160 mL respectively) to afford the tartrate (4.30 g). The salt was mixed with a saturated sodium bicarbonate solution (300 mL) and the resulting suspension was allowed to stir for 1 h and was extracted with ethyl acetate (3×300 mL). The extracts were dried, filtered and evaporated to dryness to afford the free base (2.71 g), which was treated with 2N HCl to give 2.71 g of the salt, $[\alpha]_D$ +14.7° C. (c=0.55, $H_2O$); mp 261°-263° C.

Analysis calculated for $C_9H_{16}ClN_3O_4S_3$—0.5 $H_2O$: C, 29.87; H, 4.46; N, 11.61 Found: C, 29.85; H, 4.28; N, 11.36

EXAMPLE 11

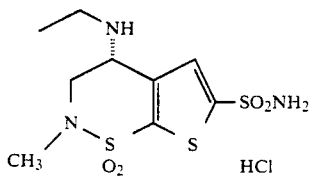

Alternative preparation of:

R-(+)-4-Ethylamino-3,4-dihydro-2-methyl-2H-thieno[3,2-e]-1,2-thiazine-6-sulfonamide 1,1-dioxide hydrochloride Step A: 3-(2,5,5-Trimethyl-1,3-dioxan-2-yl)thiophene Hydrogen chloride gas was bubbled briefly into a mixture of 3-acetylthiophene (100 g, 0.794 mol) and 2,2-dimethyl-1,3-propanediol (1.5 eq, 1.19 mol, 123 g) in toluene (650 mL) and the mixture was refluxed for 18 h with water removal using a Dean-Starck trap. Since only about half of the theoretical amount of water had been removed after this time, a few drops of concentrated sulfuric acid were added to the mixture and reflux was continued another 24 h. The mixture was allowed to cool to room temperature under a drying tube and potassium carbonate (10 g) was added followed by saturated aqueous sodium bicarbonate (300 mL) and hexane (1 L) The organic phase was separated and the aqueous was extracted with hexane (3×400 mL). The combined hexane extracts were washed with brine (6×500 mL), dried over $MgSO_4$, treated with decolorizing carbon, filtered through celite and evaporated under reduced pressure. The residue was distilled through a 12 inch Vigreux column to provide 120 g (71%) of the ketal as a colorless liquid that solidified on standing: bp 88° C./0.1 mmHg).

Step B: 3-Acetyl-N-methyl-2-thiophenesulfonamide

A solution of the compound from Step A (50.0 g, 0.236 mol) in hexane (400 mL) was cooled to −60° C. under nitrogen. n-Butyllithium (1.3 eq, 120 mL of a 2.5 M hexane solution) was added over 15 min while the temperature was maintained at −60° C. The cold bath was removed, and the reaction mixture was allowed to warm to room temperature, taking 30 min. After the mixture had stirred at room temperature for 30 min, it was again cooled to −60° C., at which point tetrahydrofuran (100 mL) was added. After the mixture had returned to −60° C., sulfur dioxide gas was bubbled into the reaction until the mixture was acidic, and the mixture was stirred overnight while warming to room temperature. N-Chlorosuccinimide (40 g, 1.3 eq) was added in one portion and stirring was continued at room temperature for 6 h. Methylamine gas was then bubbled into the mixture until the sulfonyl chloride was no longer present as indicated by TLC. (silica, 30% ethyl acetate/hexane). The reaction mixture was then concentrated on the rotary evaporator under reduced pressure, and the residue was diluted with tetrahydrofuran (400 mL) and 1 M aqueous hydrochloric acid (400 mL) and refluxed for 1 h. The mixture was then cooled, basified using solid sodium bicarbonate, and partitioned between water (1 L) and ethyl acetate (500 mL). The organic phase was separated and the aqueous layer was further extracted with ethyl acetate (3×400 mL). The combined organic layers were washed with saturated aq. sodium bicarbonate (4×500 mL), dried over $MgSO_4$, treated with decolorizing carbon, filtered through celite, and so concentrated. The residual oily solid was leached with diethyl ether (500 mL) resulting in a solid that was collected by filtration, washing with ether, to provide, after air drying, 31 g (60%) of the sulfonamide: mp 101°-103° C.

Step C:
3-Bromoacetyl-N-methyl-2-thiophenesulfonamide

A solution of the compound from Step B (71.0 g, 0.324 mol) in tetrahydrofuran (350 mL) was chilled in an ice-water bath to an internal temperature of 0°-5° C. Hydrogen chloride gas was bubbled into the solution very briefly, and then pyridinium bromide perbromide (0.9 eq, 0.291 mol, 93.0 g) was added in one portion. Within 10 min, a precipitate formed and the reaction turned orange-yellow. After 20 min, the reaction mixture was poured into ice-water (1 L), and the solid was collected by filtration, washing with water. The still moist solid was leached with ethanol (700 mL), filtered, washing first with ethanol (200 mL) and then diethyl ether (250 mL), and air dried on the funnel to provide 71 g (73%) of the bromo ketone: mp 112°-115° C.

Step D:
(+)-4-Hydroxy-2-methyl-3,4-dihydro-2H-thieno[3,2-e]-1,2-thiazine 1,1-dioxide A 5-L, jacketed flask fitted with a mechanical stirrer, a 1.L addition funnel, and a thermometer was charged with the compound from Step 6 (48.7 g, 0.163 mol) and tetrahydrofuran (3 L) under nitrogen, and the mixture was cooled to −25° C. with the aid of a refrigerated circulator. A solution of (+)-β-chlorodiisopinocampheylborane (2 eq, 0.326 mol, 105 g) in tetrahydrofuran (500 mL) was prepared in a separate flask and transferred into the addition funnel using a cannula. It was then added to the ketone solution at a rate such that the internal temperature did not exceed −24° C. (about 1 h was required). The reaction mixture was stirred at −25° C. for 7. h and then allowed to warm to room temperature before it was decanted into a 3-L flask. The tetrahydrofuran was removed on the rotary evaporator under reduced pressure and diethyl ether (1 L) was added to the pale yellow residue. Diethanolamine (2 eq, 34.2 g) was added, and the mixture was stirred with a mechanical stirrer for 2 h. The mixture was filtered through a sintered glass filter, and the white precipitate was collected and stirred with ether (250 mL). After filtration, the combined ether filtrates were concentrated on the rotary evaporator under reduced pressure. The residue was dissolved in 1:1 acetone/water (1 L), 1 M aq. sodium hydroxide (30–40 mL) was added, and the solution was heated at 45° C. for 2 h. Removal of the acetone at 40 mmHg left an aqueous solution which was extracted with ethyl acetate (3×100 mL). The combined extracts were dried over $Na_2SO_4$, and the ethyl acetate was removed on the rotary evaporator under reduced pressure. The residue was taken up in acetonitrile (500 mL), and this solution was extracted with hexane (3×100 mL) before the acetonitrile was removed under reduced pressure. The residue was dissolved in 50% ethyl acetate/hexane and applied to a 1.5 L bed of 230-400 mesh silica gel in a 3-L sintered glass funnel. Elution first with 30% ethyl acetate/hexane (3 L) and then ethyl acetate (5 L) provided, after solvent removal, 32.8 g (92%) of the alcohol as a viscous orange oil that solidified on standing. The enantiomeric excess was determined to be 94% using a chiral chromatography method.

Step E:
(+)-4-Hydroxy-2-methyl-3,4-dihydro-2H-thieno[3,2-e]-1,2-thiazine-6-sulfonamide 1,1-dioxide A solution of the compound from Step D (53.3 g, 0.243 mol) in tetrahydrofuran (1.7 L) in a 3-L, 3-neck flask equipped with a mechanical stirrer, a 500 mL addition funnel, and a thermometer was cooled to -75.C. using a dry-ice/acetone bath. n-Butyllithium (2.2 eq, 0.535 mol, 215 mL of a 2.5 M hexane solution) was added over about 30 min while the temperature was maintained below −72° C. The solution was allowed to warm to 0° C. for 2 h and then cooled again to −72° C. The addition funnel was replaced with a gas inlet tube and sulfur dioxide gas was added as rapidly as possible until the pH remained below 6 for at least 1 minute. The mixture was allowed to warm to room temperature, decanted into a 3-L flask, and concentrated on the rotary evaporator under reduced pressure. The residue was dissolved in water (500 mL) and sodium acetate (59.8 at 0.729 mol) was added, followed by hydroxylamine-O-sulfonic acid (49.5 at 0.437 mol). The solution was stirred for 16 h at room temperature before the pH was adjusted to 7-8 by the cautious addition of solid sodium bicarbonate. The solution was extracted with ethyl acetate (3×100 mL) and the combined extracts were concentrated under reduced pressure. The residue was dissolved in 1 M aq. sodium hydroxide (100 mL), and the solution was washed with ethyl acetate (3×50 mL), adjusted to pH 6-7 by the cautious addition of 6 M aq. hydrochloric acid, and extracted with ethyl acetate (3×100 mL). The combined extracts were dried over $Na_2SO_4$ and concentrated under reduced pressure. The viscous oil that remained was dissolved in a minimum amount of warm ethyl acetate (<50 mL) and the product precipitated by the addition of methylene chloride (about 250 mL). This procedure was repeated twice on the concentrated mother liquor. The off-white solid collected by filtration from each of these operations was air dried and combined to provide 52.1 g (72%) of the sulfonamide: mp 168° C.

Step F:
(+)-4-Ethylamino-3,4-dihydro-2-methyl-2H-thieno[3,2-e]-1,2-thiazine-6-sulfonamide 1,1-dioxide Under nitrogen, a stirred solution of the compound from Step E (5.00 g, 16.8 mmol) and p-toluenesulfonyl chloride (1.1 eq, 18.5 mmol, 3.30 g) in tetrahydrofuran (100 mL) was treated with triethylamine (1.1 eq, 2.78 mL). After 18 h at room temperature, TLC. indicated that starting material was still present so additional p-toluenesulfonyl chloride (0.4 eq, 1.3 g) and triethylamine (0.4 eq, 1.0 mL) was added. Stirring was continued for another 18 h, at which point TLC. indicated the absence of starting material. Ethylamine (18 g) was added to the reaction mixture and the flask was stoppered. After 18 h at room temperature, TLC. indicated that the intermediate tosylate was absent. At this point, the reaction mixture was combined with another 1.55 g run for workup. The mixture was partitioned between 1 M aqueous hydrochloric acid (100 mL) and diethyl ether (250 mL) and the acidic aqueous phase was separated. The organic phase was further extracted with 1 M aqueous hydrochloric acid (3×100 mL), and the combined aqueous layers were then back washed with ether (3×100 mL), basified using solid sodium bicarbonate, and extracted with ethyl acetate (4×250 mL). The combined organic ethyl acetate extracts were dried over MgSO₄, treated with decolorizing carbon (Norite A), filtered through celite, and concentrated under reduced pressure, to provide 5.2 g (73%) of the sulfonamide.

Step G:
(+)-4-Ethylamino-3,4-dihydro-2-methyl-2H-thieno[3,-2.e]-1,2-thiazine-6-sulfonamide 1,1-dioxide The compound from Step F (27.0 g, 83.1 mmol) (94% ee) was dissolved in n-propanol (800 mL) and the solution was filtered through a sintered glass filter. The filtrate was heated to about 80° C., and an 80° C. solution of di-p-toluoyl-D-tartaric acid (15.7 g, 40.7 mmol) in n-propanol (500 mL) was added. The mixture was allowed to stand at room temperature overnight before it was cooled in an ice-water bath for 1 h. The crystals were collected by filtration, washed with cold n-propanol, and dried to provide 39.2 g (93%) of the di-p-toluoyl-D-tartrate salt of greater than 98% ee. Because this material was somewhat colored, it was recrystallized from n-propanol (1.5 L) to provide a first crop of 34.8 g. This solid was added to a saturated aqueous solution of sodium bicarbonate (500 mL), and the mixture was stirred for 1 h. The mixture was then extracted with ethyl acetate (4×400 mL), and the combined extracts were dried over 4A molecular sieves, filtered, and concentrated on the rotary evaporator at reduced pressure to provide 20.2 g (75% recovery) of the (+)-sulfonamide of greater than 98% ee.

Step H:
(+)-4-Ethylamino-3,4-dihydro-2-methyl-2H-thieno[3,2-e]-1,2-thiazine-6-sulfonamide 1,1-dioxide hydrochloride The compound from Step G (20.2 g, 62.2 mmol) was treated with 2 M ethanolic hydrogen chloride (40 mL), and then the mixture was evaporated to dryness under reduced pressure. The residue was dissolved in water (200 mL) and evaporated to dryness to provide the hydrochloride salt which was washed with ethyl acetate and dried under high vacuum at 78° C. for 6 h. The yield of the hydrochloride salt was 21.7 g (94%) as the hemihydrate.

Example 12

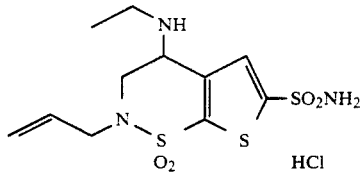

2-Allyl-4-ethylamino-3,4-dihydro-2H-thieno[3,2-e]-1,2-thiazine-6-sulfonamlde 1,1-dioxide hydrochloride Step A:
2-Allyl-3,4-dihydro-4-hydroxy-2H-thieno[3,2-e]-1,2-thiazine 1,1-dioxide The product from Step C of Example 2 (4.0 g, 19.5 mmol) was dissolved in anhydrous DMF (70 mL) cooled to −10° C. and sodium hydride (21.5 mmol) was added. After stirring for five minutes allyl bromide (2.53 mL, 29.25 mmol) was added and this mixture stirred for 2 h at 0° C. The reaction mixture was poured onto ice water (100 mL) and this solution was extracted with ethyl acetate. The combined extracts were washed with brine, dried (MgSO₄) and evaporated to give a crude product which was purified by column chromatography (silica, methylene chloride:methanol, 20:1) to provide the desired product (4.2 g, 88%) as a syrup.

Step B:
2-Allyl-4-(1-ethoxy)ethoxy-3,4-dihydro-2H-thieno[3,2-e]-1,2-thiazine 1,1-dioxide The product from Step A (4.2 g, 17.1 mmol) was dissolved in tetrahydrofuran (75 mL) and cooled to 0° C. at which point p-toluenesulfonic acid (163 mg, 0.6 mmol) was added followed by ethylvinyl ether (3.3 mL, 34.3 mmol). This mixture was stirred at 0° C. for 2 h, diluted with cold ethyl acetate (100 mL) and washed with saturated sodium bicarbonate (70 mL) and brine (70 mL). The organic layer was dried (MgSO₄) and evaporated to provide 5.2 g of crude product which was used in the next step without further purification.

Step C:
2-Allyl-3,4-dihydro-4-hydroxy-2H-thieno[3,2-e]-1,2-thiazine-6-sulfonamide 1,1-dioxide The product from Step B (5.0 g, 15.8 mmol), dissolved in anhydrous tetrahydrofuran (125 mL) and cooled to −60° C., was treated dropwise with n-butyllithium (2.5 M, 7.6 mL, 18.9 mmol). This mixture was stirred at −40° C. for 40 min and then sulfur dioxide gas was bubbled over the surface for 20 min after which time the mixture was warmed to room temperature. After 30 min at room temperature the mixture was concentrated and the residue was dissolved in water (150 mL), cooled to 0° C. and sodium acetate trihydrate (6.4 g, 47.3 mmol) was added followed by hydroxylamine-O-sulfonic acid (3.2 g, 28.4 mmol). The reaction mixture was stirred at room temperature for 18 h after which time was basified with solid sodium bicarbonate and extracted with ethyl acetate. The combined extracts were washed with saturated sodium bicarbonate solution, dried (MgSO₄) and the solvent evaporated to give the desired intermediate (5.0 g). This residue was dissolved in tetrahydrofuran (70 mL), cooled to 0° C. and then 1N HCl (70 mL) was added. After stirring at room temperature for 1 h the tetrahydrofuran was evaporated and the solution was neutralized with saturated sodium bicarbonate solution. The product was extracted into ethyl acetate and the combined extracts were dried (MgSO₄) and evaporated to a residue which was purified by chromatography (silica, 5% methanol:methylene chloride) to give a syrup (1.2 g).

Step D: 2 - Allyl-4-ethylamino-3,4-dihydro-2H-thieno[3,2-e]-1,2-thiazine-6-sulfonamide 1,1-dioxide hydrochloride The product from Step C (1 g, 3 mmol) was dissolved in tetrahydrofuran (50 mL) containing triethylamine (1.7 mL, 12.0 mmol) and the solution was cooled to −16° C. Tosyl chloride (1.1 g, 6.0 mmol) was added and the mixture stirred for 18 h at room temperature after which time it was cooled to 0° C. and ethylamine (10 mL) was added. After heating at reflux for 1 h the solvent was evaporated and the residue dissolved in ethyl acetate (50 mL) and washed with 1N HCL (3×20 mL). The combined aqueous washes were basified (sodium bicarbonate) and extracted with ethyl acetate. The combined extracts were washed with saturated sodium bicarbonate solution (3×15 mL) and brine (3×15 mL), dried (MgSO₄) and evaporated to give the desired free base (620 mg) as a syrup. This material was dissolved in ethanol (5 mL) and 1N ethanolic HCL (5 mL) was added. This solution was then concentrated to dryness to give the desired product as a light yellow solid (400 mg): mp 243°–245° C.

Analysis calculated for $C_{11}H_{18}ClO_4N_3S_3$: C,34.06; H, 4.68; N, 10.83 Found: C,34.00; H, 4.42; N, 10.71

EXAMPLE 13

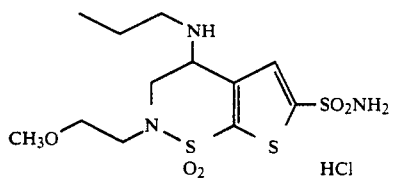

3,4-Dihydro-2-(2-methoxy)ethyl-4-proplyamino-2H-thieno[3,2-e]-1,2-thiazine-6-sulfonamide 1,1-dioxide hydrochloride Step A:
3,4-Dihydro-4-hydroxy-2-(2-methoxy)ethyl-2H-thieno[3,2-e]-1,2-thiazine 1,1-dioxide A solution of the product form Step C of Example 2 (19.2 g, 0.093 mol) in DMF (125 mL) was added to a suspension of sodium hydride (3.08 g, 80% oil dispersion, 0.103 mol) in DMF at 006. When the addition was completed the ice bath was removed and the reaction mixture stirred at ambient temperature for 1 h. The reaction mixture was cooled to 0° C. and 2-bromoethyl methylether (13.6 mL, 0.14 mol) was added. The reaction mixture was stirred at ambient temperature for 18 h after which time it was evaporated to dryness. The residue was suspended in brine (100 mL) and extracted with methylene chloride (4×80 mL). The combined extracts were dried ($MgSO_4$), filtered and evaporated to a solid which was recrystallized from ethyl acetate to give the desired subject (17.4 g). Chromatography of the mother liquor (silica, 3% ethanol:methylene chloride) furnished more subject which was combined with the first batch to give a total of 19.3 g (78%) of the product.

Step B:
4-(1-Ethoxy)ethoxy-3,4-dihydro-2-(2-methoxy)ethyl-2H-thieno[3,2-e]-1,2-thiazine 1,1-dioxide Using essentially the same procedure described in Example 12, Step B, the product from Step A (4.9 g, 18.6 mmol) was converted to the subject compound (6.2 g, 99%).

Step C:
3,4-Dihydro-4-hydroxy-2-(2-methoxy)ethyl-2H-thieno[3,2-e]-1,2-thiazine-6-sulfonamide 1,1-dioxide By using a procedure similar to that described in Example 12, Step C, the product from Step B (6.2 g, 18.4 mmol) was converted into the subject compound (4.87 g, 77%): mp 187° C.

Step D:
3,4-Dihydro-2-(2-methoxy)ethyl-4-propylamino-2H-thieno[3,2-e]-1,2-thiazine-6-sulfonamide 1,1-dioxide hydrochloride Using essentially the same procedure described in Example 12, Step D, but employing the product of Step C of this Example (1.0 g, 2.92 mmol) and propylamine instead of ethylamine, the desired product (0.57 g, 46%) was obtained: mp 178°–181° C.

Analysis calculated for $C_{11}H_{22}ClN_3O_5S_3$: C, 34.32; H, 5.28; N, 10.01 Found: C, 34.27; H, 5.21; N, 9.94.

EXAMPLE 14

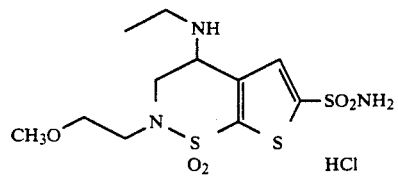

4-Ethylamino-3,4-dihydro-2-(2-methoxy)ethyl-2H-thieno[3,2-e]-1,2-thiazine-6-sulfonamide 1,1-dioxide hydrochloride By employing essentially the same procedure described in Example 13 but substituting ethylamine for propylamine in Step D the subject compound was prepared: mp 223° C.

EXAMPLE 15

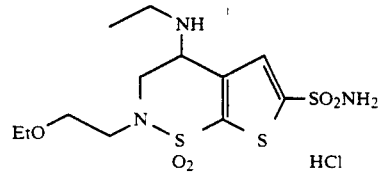

2-(2-Ethoxy)ethyl-4-ethylamino-3,4-dihydro-2H-thieno[3,2-e]-1,2-thiazine-6-sulfonamide 1,1-dioxide hydrochloride By employing essentially the same procedure described in Example 13 but substituting 2-bromoethyl ethylether for 2-bromoethyl methylether in Step A and ethylamine for propylamine in Step D the subject compound was prepared: mp 172° C.

EXAMPLE 16

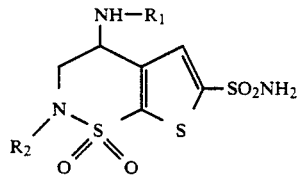

Using the procedures described in Examples 13 and 14 but substituting the appropriate alkylhaloether in Step A and the desired alkylamine in Step D the following compounds were prepared:
1: $R_1=CH_2CH_3$; $R_2=(CH_2)_3OCH_3$: 4-Ethylamino-3,4-dihydro-2-(3-methoxy)propyl-2H-thieno[3,2-e]-1,2-thiazine-6-sulfonamide-1,1-dioxide hydrochloride mp 203°–205° C;
2: $R_1=CH_2CH_3$; $R_2=(CH_2)_2O(CH_2)OCH_3$: 4-Ethylamino-3,4-dihydro-2-[2-(methoxy ethoxy)ethyl]-2H-thieno[3,2-e]-1,2-thiazine-6-sulfonamide-1,1-dioxide hydrochloride: mp 194°–196° C.;

3: $R_1 = (CH_2)_2CH_3$; $R_2 = (CH_2)_2O(CH_2)_2OCH_3$: 3,4-Dihydro-4-propylamino-2-[2-(methoxyethoxy)ethyl]-2H-thieno[3,2-e]-1,2-thiazine-6-sulfonamide-1,1-dioxide hydrochloride: mp 174°–178° C.;

4: $R_1 = CH_2CH_3$; $R_2 = (CH_2)_3O(CH_2)_2OCH_3$: 4-Ethylamino-3,4-dihydro-2-[3-(2-methoxy)ethoxy]propyl-2H-thieno[3,2-e]-1,2-thiazine-6-sulfonamide-1,1-dioxide hydrochloride: mp 209°–211° C.;

5: $R_1 = (CH_2)_2CH_3$; $R_2 = (CH_2)_3O(CH_2)_2OCH_3$: 3,4-Dihydro-4-propylamino-2-[3-(2-methoxy)ethoxy)propyl]-2H-thieno[3,2-e]-1,2-thiazine-6-sulfonamide-1,1-dioxide maleate: mp 150°–152° C.

Using the procedures described in Examples 13 and 14 but substituting the appropriate alkylhaloether in Step A and the desired alkylamine in Step D the following compounds can be prepared:

6: $R_1 = (CH_2)_2CH_3$; $R_2 = (CH_2)_2OCH_2CH_3$: 2-(2-Ethoxy)ethyl-3,4-dihydro-4-propyl amino-2H-thieno[3,2-e]-1,2-thiazine-6-sulfonamide-1,1-dioxide hydrochloride;

7: $R_1 = CH_2CH_3$; $R_2 = (CH_2)_3OCH_2CH_3$: 2-(3-Ethoxy)propyl-4-ethylamino-3,4-dihydro-2H-thieno[3,2-e]-1,2-thiazine-6-sulfonamide-1,1-dioxide hydrochloride.

8: $R_1 = (CH_2)_2CH_3$; $R_2 = (CH_2)_3OCH_3$: 3,4-Dihydro-2-(3-methoxy)propyl-4-propyl amino-2H-thieno[3,2-e]-1,2-thiazine-6-sulfonamide-1,1-dioxide hydrochloride.

EXAMPLE 17

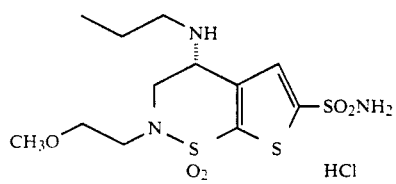

R-(+)-3,4-Dihydro-2-(2-methoxy)ethyl-4-propylamino-2H-thieno[3,2-e]-1,2-thiazine-6-sulfonamide 1,1-dioxide hydrochloride Step A:
3,4-Dihydro-2-(2-methoxy)ethyl-4-oxo-2H-thieno[3,2-e]-1,2-thiazine-6-sulfonamide 1,1-dioxide To a solution of the product of Example 13, Step C (1.0 g, 2.92 mmol), in acetone (65 mL) was added over 3 min Jones reagent (1.1 M, 2.66 mL, 2.92 mmol). After 20 min the mixture was evaporated to dryness and the residue was triturated with ethyl acetate (3×80 mL) and the combined organics were washed with brine and dried over molecular sieves. Concentration gave the desired product (0.92 g).

Step B: (−)-3,4-Dihydro-4-hydroxy-2-(2-methoxy)ethyl-2H-thieno[3,2-e]-1,2-thiazine-6-sulfonamide 1,1-dioxide To a solution of the product from Step A (550 mg, 16.2 mmol) in tetrahydrofuran (200 mL) cooled to −65° C. was added dropwise a solution of (+)-β-chlorodiisopinocampheyl borane (25.6 g, 79.8 mmol) in anhydrous tetrahydrofuran (30 mL) over 5 min. After the addition was completed the mixture was stored at −22° C. for 3 days. Diethanolamine (11.06 g, 105.2 mmol) was added and the mixture stirred for 30 min and then evaporated to dryness. The residue was mixed with a saturated solution of sodium bicarbonate (100 mL) and extracted with ethyl acetate (3×150 mL). Concentration of the organics gave a viscous liquid which was chromatographed (silica, hexane to 50% hexane:ethyl acetate to 10% methanol:methylene chloride) to give the desired subject (5.23 g, 95%): mp 131°–133° C.; $[\alpha]_D$ −3.31° (C- 1.18, MeOH).

Step C:
(+)-3,4-Dihydro-2-(2-methoxy)ethyl-4-propylamino-2H-thieno[3,2-e]-1,2-thiazine-6-sulfonamide 1,1-dioxide hydrochloride To a solution of the product form Step B (2.68 g, 784 mmol) and triethylamine (3.19 g, 31.3 mmol) in anhydrous tetrahydrofuran (100 mL) cooled to −20° C. was added tosyl chloride (2.99 g, 15.7 mmol) over 5 min. This mixture was placed in an ice bath for 18 h and after which time an excess of propylamine (10.0 g, 169 mmol) was added. The mixture was stirred at ambient temperature for 1 h followed by heating at reflux for an additional 2 h. Evaporation of the mixture gave a crude product which was mixed with saturated sodium bicarbonate (100 mL) and extracted with ethyl acetate (3×100 mL) The combined extracts were evaporated and the residue chromatographed (silica, 5% methanol:methylene chloride) to give the free base (1.7 g, 57%). The free base was dissolved in ethyl acetate (20 mL) and treated with a solution of 1.5 N ethanolic HCl in ethanol (4.5 mL). The solution was evaporated to dryness and the residue dissolved in methanol (2 mL) and methylene chloride (80 mL) was added. After crystallization was complete the solid was collected and dried (65° C. in vacuo) to give the desired product (1.45 g, 36%): mp 205°–206° C.; $[\alpha]_D$ +6.02° (C=1.03, H_2O).

Analysis calculated for $C_{12}H_{22}ClN_3O_5S_3$: C, 34.31; H, 5.27; N, 10.01 Found: C, 33.99; H, 5.12; N, 9.81

Example 18

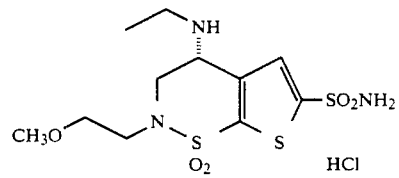

R-(+)-4-Ethylamino-3,4-dihydro-2-(2-methoxy)ethyl-2H-thieno[3,2-e]- 1,2-thiazine-6-sulfonamide 1,1-dioxide hydrochloride Using essentially the same procedure as described in Example 17 except substituting an equimolar amount of ethyl amine for propylamine the desired subject is produced: mp 224°–227° C.: $[\alpha]_D$ +5.86° (C=1.11, H_2O).

Analysis calculated for C, 31.84; H, 5.10; N, 10.13 Found: C, 31.97; H, 4.97; N, 10.15

EXAMPLE 19

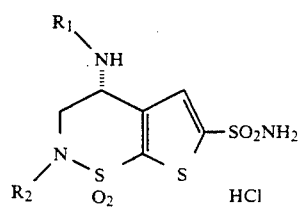

As in Example 16, using the chiral reduction procedure described in Example 17, Steps A and B, except substituting the 2-substituents of the compounds in Example 16, A through G, and employing the displacement reaction described in Example 17, Step C, yet substituting the requisite alkylamine, the isomers with the desired (R) absolute configuration of the 4-position can be prepared.

1: $R_1=CH_2CH_3$; $R_2=(CH_2)_3OCH_2CH_3$: (R)-2-(3-Ethoxy)propyl-3,4-dihydro-4-ethylamino-2H-thieno[3,2-e]-1,2-thiazine-6-sulfonamide hydrochloride;

2: $R_1=(CH_2)_2CH_3$; $R_2=(CH_2)_3OCH_2CH_3$: (R)-2-(3-Ethoxy)propyl-3,4-dihydro-4-propylamino-2H-thieno[3,2-e]-1,2-thiazine-6-sulfonamidehydrochloride;

3: $R_1=(CH_2)_2CH_3$; $R_2=(CH_2)_3OCH_3$: (R)-3,4-Dihydro-2-(3-methoxy)propyl-4-propylamino-2H-thieno[3,2-e]-1,2-thiazine-6-sulfonamide 1,1-dioxide hydrochloride;

4: $R_1=CH_2CH_3$; $R_2=(CH_2)_2O(CH_2)_2OCH_3$: (R)-4-Ethylamino-3,4-dihydro-2-[2-(methoxyethoxy)ethyl]-2H-thieno[3,2-e]-1,2-thiazine-6-sulfonamide 1,1-dioxide hydrochloride;

5: $R_1=(CH_2)_2CH_3$; $R_2=(CH_2)_2O(CH_2)_2OCH_3$: (R)-3,4-Dihydro-2-[2-(methoxyethoxy)ethyl]-4-propylamino-2H-thieno[3,2-e]-1,2-thiazine-6-sulfonamide 1,1-dioxide hydrochloride;

6: $R_1=CH_2CH_3$; $R_2=(CH_2)_3O(CH_2)_2OCH_3$: (R)-4-Ethylamino-3,4-dihydro-2-[3-(2-methoxy)ethoxy]propyl-2H-thieno[3,2-e]-1,2-thiazine-6-sulfonamide 1-dioxide hydrochloride;

7: $R_1 (CH_2)_2 CH_3$; $R_2=(CH_2)_3O(CH_2)_2OCH_3$: (R)-3,4-Dihydro-2-[3-(methoxyethoxy)propyl]-4-propylamino-2H-thieno[3,2-e]-1,2-thiazine-6-sulfonamide 1,1-dioxide hydrochloride.

EXAMPLE 20

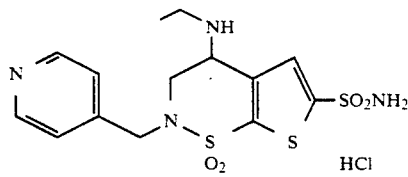

4-Ethylamino-3,4-dihydro-2-(4-pyridinyl)methyl-2H-thieno[3,2-e]-1,2-thiazine-6-sulfonamide 1,1-dioxide hydrochloride

Step A:
3,4-Dihydro-4-hydroxy-2-(4-pyridinyl)methyl-2H-thieno[3,2-e]-1,2-thiazine 1,1-dioxide The product from Step C of Example 2 (4.0 g, 19.5 mmol) was dissolved in anhydrous DMF (20 mL) and cooled to −10° C. and sodium hydride (21.5 mmol) was added. After stirring for 40 min at room temperature, a solution of 4-picolyl chloride (3.7 g, 29.2 mmol) in DMF (15 mL) was added to the chilled (0° C.) reaction mixture. The mixture was allowed to warm to room temperature and stir for 18 h. The solution was concentrated and the residue was suspended in saturated sodium bicarbonate (50 mL) and the desired subject was collected by filtration. Recrystallization from ethanol gave a beige solid (4.9 g, 85%): mp 183°–185° C.

Step B:
4-Ethylamine-3,4-dihydro-2-(4-pyridinyl)methyl-2H-thieno[3,2-e]-1,2-thiazine ],1-dioxide The product from Step A (4.8 g, 16.2 mmol) was dissolved in DMF (50 mL) and triethylamine (2.49 mL) and 4-N,N-dimethylaminopyridine (0.11 g) were added. The mixture was cooled (5° C.) and methane sulfonic anhydride (3.1 g, 17.8 mmol) was added and the mixture stirred at room temperature for 3 h followed by heating at 50° C. for 1.5 h. The reaction mixture was cooled, concentrated and the residue was dissolved in tetrahydrofuran (25 mL) and aqueous ethylamine (50 mL) was added. The mixture stirred for 18 h at room temperature after which time it was concentrated and the residue was dissolved in a minimum amount of methylene chloride and chromatographed (silica, 4% ethanol to 6% ethanol:methylene chloride) to give the desired subject as a syrup (3.0 g, 57%).

Step C:
4-Ethylamino-3,4-dihydro-2-(4-pyridinyl)methyl-2H-thieno[3,2-e]-1,2-thiazine-6-sulfonamide 1,1-dioxide A mixture of the product from Step B (0.55 g, 1.7 mmol) and chlorosulfonic acid (2 mL) was heated to 45° C. for 4 h. After cooling the reaction mixture was added dropwise to cold 30% ammonium hydroxide (12 mL) while maintaining the temperature below 10° C. The solid was collected and dissolved in ethanol (50 mL), concentrated to 10 mL and filtered. Treatment of this solution with 1.5 N ethanolic HCl provided a solid which was collected and dried to give the subject (0.38 g, 47%): mp 164°–169° C.

EXAMPLE 21

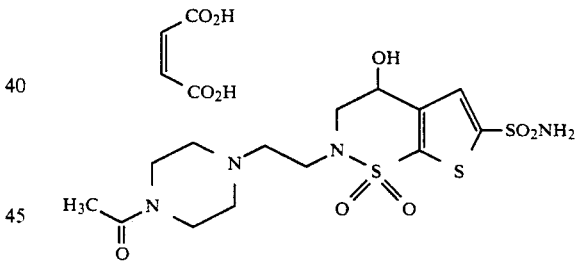

2-[1-(4-Acetyl-piperazinyl)]ethyl-3,4-dihydro-4-hydroxy-2H-thieno[3,2-e]-1,2-thiazine-6-sulfonamide-1,1-dioxide maleate

Step A:
3,4-Dihydro-4-hydroxy-2H-thieno[3,2-e]-1,2-thiazine-6-(N-t-butyl)sulfonamide-1,1-dioxide To a solution of the product from Example 2, Step C (6.25g, 30 mmol) in THF (40 mL) at 0° C. was added p-toluenesulfonic acid (200 mg) and ethylvinyl ether (10.3 mL, 0.107 mol). The mixture was stirred for 6 hr at 0° C. followed by the addition of an aqueous solution of NaHCO$_3$ (100 mL). The organic layer was separated and the aqueous layer was extracted with EtOAc (3×50 mL). The extracts were combined, washed with brine (30 mL), dried (MgSO$_4$) and evaporated to give an oil which was purified by column chromatography (silica; 30% EtOAc/hexane) to give the desired protected intermediate product (10.1 g, 99%). To a solution of this material (9.60 g, 28 mmol) in THF (60 mL) was added a solution of n-butyllithium in pentane (20.6 mL of a 2.0 M solution) at −78° C. over a period of 20 minutes. After stirring this solution for 45 min, a stream of SO₂ gas was passed over the surface of the solution (20 min). The reaction mixture was allowed to warm to room temperature and stirred at this temperature for 2 hr. The reaction mixture was allowed to warm to room temperature and stirred at this temperature for 2 hr. The solvent was evaporated to give a residue which was dissolved in methylene chloride (200 mL), cooled to 0° C., and N-chlorosuccinamide (7.4 g, 0.055 mol) was added in portions. After one hour the reaction mixture was allowed to warm to room temperature; stirring continued for two more hours, at which point the methylene chloride was removed by evaporation and the residue dissolved in THF (100 mL). This solution was cooled (0° C.) and a solution of t-butylamine (7.8 mL, 0.075 mol) in THF (50 mL) was added dropwise followed by stirring for 8 hr at room temperature. After removal of excess amine by evaporation, 2N HCl (10 mL) was added and the reaction mixture stirred at room temperature for 8 hr. Water (50 mL) was added and the organic layer separated. The aqueous layer was extracted with ethyl acetate (3×100 mL) and the combined organic layers were washed with brine (30 mL), dried (MgSO₄), and evaporated to provide crude product which was purified by column chromatography (silica; 5% CH₃OH/CH₂Cl₂) to give the desired product as a yellow syrup (7.3 g, 72%).

Step B:
2-(2-Bromoethyl)-3,4-dihydro-4-hydroxy-2H-thieno3,2-e]-1,2-thiazine-6-(N-t-butyl)-sulfonamide-1,1-dioxide To a suspension of NaH (1.9 g, 0.049 mol) in DMF (10 mL) was added a solution of the product from Step A (8.3 g, 24.4 mmol) in DMF (20 mL) at 0° C. This mixture was stirred for 40 minutes and 1,2-dibromoethane (8.34 mL, 0.098 mol) was added dropwise after which the reaction mixture was stirred for 4 hr at room temperature. A saturated aqueous solution of ammonium chloride (20 mL) was added and the mixture extracted with ethyl acetate (3×100 mL). The combined extracts were washed with brine (50 mL), dried (MgSO₄) and evaporated to give an oil which was purified by chromatography (silica; 50% ethyl acetate/hexane) to give 8.8 g (81%) of the desired product.

Step C:
2-[1-(4-Acetyl-piperazinyl)ethyl-3,4-dihydro-4-hydroxy-2H-thieno-[3,2-e]-1,2-thiazine-6-sulfonamide-1,1-dioxide maleate To a solution of the product from Part B (2.02 g, 4.5 mmol) in 3-methyl-2-butanone (15 mL) was added 1-acetylpiperazine (2.23 g, 17.5 mmol), sodium carbonate (1.8 g, 17.5 mmol), and potassium iodide (200 mg); this mixture was heated at 95° C. for 4 hr. The solvent was evaporated and a saturated aqueous solution of ammonium chloride (30 mL) was added to the residue. This solution was extracted with ethyl acetate (3×50 mL) and the combined extracts were washed with brine (30 mL), dried (MgSO₄), and evaporated to give an oil which was dissolved in trifluoroacetic acid (20 mL). After stirring at room temperature for 24 hr, the trifluoroacetic acid was removed by evaporation and the residue dissolved in a saturated aqueous solution of sodium bicarbonate (30 mL) which was extracted with ethyl acetate (3×50 mL). The combined extracts were washed with brine (30 mL), dried (MgSO₄), and evaporated to give an oil which was purified by column chromatography (silica; 10% CH₃OH/CH₂Cl₂) to give 1.2 g (60%) of free base. The free base (500 mg, 1.12 mmol) was dissolved in THF (10 mL) and added to a solution of maleic acid (172 mg, 1.48 mmol) in ether (10 mL). The solid which readily formed was collected by filtration, washed with an excess of ether, and dried to give the desired salt; mp 210° C. Analysis. Calculated for C₁₈H₂₆N₄O₁₀S₃H₂O: C,37.75; H, 4.93; N,9.78. Found: C,37.77; H,4.88; N,9.74.

The 2-bromoethyl derivative described in Step B or analogous compounds such as that described in Example 25, Step A, or their corresponding acetals (represented by the compound in Example 25, Step B) are key starting materials for the incorporation of a number of the heterocyclic rings found in the novel compounds of Structure [1]. Many of the simplified rings which correspond to the general structure of NR₅-R₆ where R₅ and R₆ form a 5 or 6 member ring can be obtained commercially. In other cases the desired heterocyclic component can be prepared from these simplified rings or by other methods which are known to one skilled in the art. Important lead references which disclose the synthesis of these heterocyclic rings are: "Comprehensive Heterocyclic Chemistry," A. R. Katritzky et al., Volumes 2-6, and references cited therein.

EXAMPLE 22

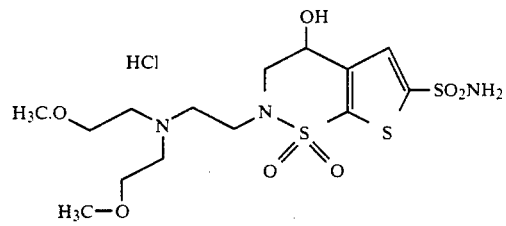

3,4-Dihydro-hydroxy-2-[2-(N,N-dimethoxyethyl)aminoethyl]-2H-thieno-[3,2-e]-1,2-thiazine-6-sulfonamide-1,1-dioxide hydrochloride To a solution of the product from Example 21, Part B (1.70 g, 4.0 mmol) in 3-methyl-2-butanone (10 mL) was added bis(2-methoxyethyl)amine (2.2 mL, 11.0 mmol), sodium carbonate (1.2 g, 11.0 mmol), and potassium iodide (200 mg); this mixture was heated at 100° C. for 8 hr. The solvent was evaporated and water (50 mL) was added to the residue. This solution was extracted with ethyl acetate (3×50 mL) and the combined extracts were washed with brine (30 mL), dried (MgSO₄), and evaporated to give an oil which was dissolved in trifluoroacetic acid (24 mL). After stirring at 45° C. for 20 hr, the trifluoroacetic acid was removed by evaporation and the residue dissolved in a saturated aqueous solution of sodium bicarbonate (50 mL) which was extracted with ethyl acetate (3×50 mL). The combined extracts were washed with brine (30 mL), dried (MgSO₄), and evaporated to give an oil which was purified by column chromatography (silica; 10% CH₃OH/CH₂Cl₂) to give 1.1 g (58%) of free base. The free base (460 mg, 1.04 mmol) was dissolved in ethanol (10 mL) to which a solution of hydrochloric acid in ethanol (5 mL) was added; this solution was stirred for 30 min and evaporated. The solid was recrystallized (CH₃OH/Et₂O) to give the desired salt; mp 205° C.

Analysis. Calculated for $C_{14}H_{26}ClN_3O_7S_3$: C, 35.03; H, 5.46; N, 8.75. Found: C, 35.12; H, 5.44; N, 8.70.

EXAMPLE 23

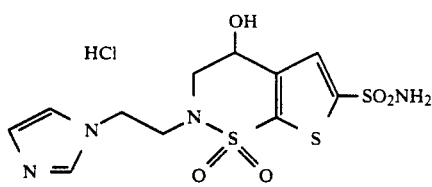

3,4-Dihydro-4-hydroxy-2-2-imidazol-1-yl)ethyl-2H-thieno[3,2-e]-1,2-thiazine-6-sulfonamide-1,1-dioxide hydrochloride To a solution of the product from Example 21, Part B (1.80 g, 4.0 mmol) in 3-methyl-2-butanone (10 mL) was added imidazole (823 mg, 12.0 mmol), sodium carbonate (1.28 g, 12.0 mmol), and potassium iodide (200 mg); this mixture was heated at 100° C. for 8 hr. The solvent was evaporated and water (50 mL) was added to the residue. This solution was extracted with ethyl acetate (3×50 mL) and the combined extracts were washed with brine (30 ml), dried (MgSO4), and evaporated to give an oil which was dissolved in trifluoroacetic acid (24 mL). After stirring at 45° C. for 24 hr, the trifluoroacetic acid was removed by evaporation and the residue dissolved in a saturated aqueous solution of sodium bicarbonate (50 mL) which was extracted with ethyl acetate (3×50 mL). The combined extracts were washed with brine (30 mL), dried (MgSO4), and evaporated to give an oil which was purified by column chromatography (silica; 10% CH3OH/CH2Cl2) to give 610 mg (40%) of free base. The free base (410 mg, 1.08 mmol) was dissolved in ethanol (10 mL) to which a 2N solution of hydrochloric acid in ethanol (5 mL) was added; this solution was stirred for 30 min and evaporated. The solid was recrystallized (CH3OH/Et2O) to give the desired salt; mp 227° C. Analysis. Calculated for $C_{11}H_{15}ClN_4O_5S_3H_2O$: C, 30.51; H, 3.96; N, 12.94. Found: C, 30.76; H, 4.07; N, 12.46.

EXAMPLE 24

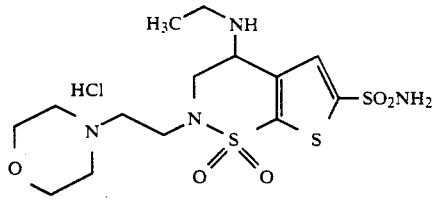

4-Ethylamino-3,4-dihydro-2-2-(4-morpholinyl)ethyl]-2H-thieno[3,2-e]-1,2-thiazine-6-sulfonamide-1,1-dioxide hydrochloride Step A:
4-Acetamido-3,4-dihydro-2-[2-(4-morpholinyl)ethyl]-2H-thieno[3,2-e]-1,2-thiazine-6-sulfonamide-1,1-dioxide To a cold (0° C.) solution of the product from Example 7 (3.9 g, 9.8 mmol) in acetonitrile (112 mL) was added concentrated sulfuric acid (33 mL) and when the addition was complete the reaction mixture was allowed to warm to room temperature. After stirring for 18 hr water (100 mL) was added to the reaction mixture and the pH was adjusted to 9 with ammonium hydroxide; this solution was extracted with ethyl acetate (5×45 mL). The combined extracts were dried (Na2SO4) and evaporated to provide crude product which was purified by column chromatography [silica; CH2Cl2/CH3OH (10:1)] to give 550 mg (12%) of the desired product: mp 110°–112° C. Analysis. Calculated for $C_{14}H_{22}N_4O_6S_3.0.5H_2O$ : C, 37.57; H, 5.17; N, 12.51, Found C, 37.31; H, 5.16; N, 12.26.

Step B:
4-Ethylamino-3,4-dihydro-2-[2-(4-morpholinyl)ethyl]-2H-thieno[3,2-e]-1,2-thiazine-6-sulfonamide-1,1-dioxide hydrochloride To a solution of the product of Step A (500 mg, 1.1 mmol) in THF (100 mL) was added a solution of BH3-SMe2 (2 mL of a 2M solution in THF) and the mixture heated at reflux temperature for 3 hr. After cooling to room temperature concentrated HCl (2 mL) was added and this solution was heated at reflux temperature for thirty minutes, cooled to room temperature and extracted with EtOAc (4×25 mL). The combined extracts were washed with a saturated aqueous solution of NaHCO3 (3×20 mL), dried (MgSO4), and evaporated to a syrup which was purified by column chromatography [silica; CH2Cl2/CH3OH (10:1)] to give s the free base as a syrup (200 mg). The free base was dissolved in a 2M solution of hydrochloric acid in ethanol (5 mL), stirred at room temperature for 20 min and the solvent was evaporated to give a solid which was recrystallized from methanol/methylene chloride to give the desired salt (60 mg, 30%): mp 218°–220° C. Analysis. Calculated for $C_{14}H_{25}Cl_2N_4O_5S_3\cdot1.0\ H_2O$: C, 37.57; H, 5.17; N, 12.51. Found: C, 37.31; H, 5.16; N, 12.26.

EXAMPLE 25

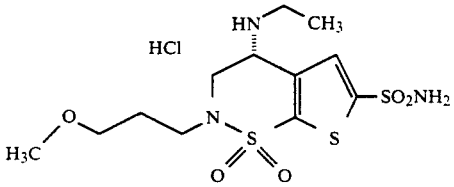

(−)-4-Ethylamino-3,4-dihyro-2-(3-methoxy)propyl-2H-thieno[3,2-e]-1,2-thiazine-6-sulfonamide-1,1-dioxide hydrochloride Step A:
2-(3-Bromo)propyl-3,4-dihydro-4-hydroxy-2H-thieno[3,2-e]-1,2-thiazine The product from Example 2, Step C (8.0 g, 39.0 mmol) was dissolved in anhydrous DMF (100 mL), cooled to −20° C. and sodium hydride (1.87 g, 46.8 mmol) was added. After stirring for five minutes, 1,3-dibromopropane (20 mL, 19.5 mmol) was added and the reaction mixture stirred for 3 hr at 0° C. The reaction mixture was diluted with ice water (100 mL) and this solution was extracted with ethyl acetate (3×30 mL). The comined extracts were washed with brine (30 mL), dried (MgSO4), and evaporated to give a crude product which was purified by column chromatography [silica; CH3OH/CH2Cl2(20:1)] to provide the desired product (10.1 g, 79%) as a syrup.

Step B:
2-(3-Bromo)propyl-4-(1-ethoxy)ethoxy-3,4-dihydro-2H-thieno-[3,2-e]-1,2-thiazine The product from Step A (10.1 g, 30.1 mmol) and p-toluenesulfonic acid (1.1 g) were dissolved in THF (100 mL) and cooled to −20° C. at which point ethylvinyl ether (5.8 mL, 60.2 mmol) was added. This mixture was allowed to warm to 0° C. and kept at this temperature for 1.5 hr followed by dilution with cold ethyl acetate (200 mL). The organic layer was separated, washed with saturated sodium bicarbonate (3×50 mL) and brine (50 mL), dried (MgSO$_4$), and evaporated to provide 9.5 g (79%) of crude product which was used in the next step without further purification.

Step C:
4-(1-Ethoxy)ethoxy-3,4-Dihydro-2-(3-methoxy)propyl-2H-thieno[3,2-e]-1,2-thiazine The product from Step B (9.5 g, 23.8 mmol) was dissolved in methanol (200 ml) and sodium methoxide (6.5 g, 119 mmol) was added; the mixture was heated at reflux temperature for 18 hr. Evaporation of the solvent gave the crude product which was dissolved in ethyl acetate (300 mL). This solution was washed with water (3×50 mL) and brine (3×35 mL), dried (MgSO$_4$) and evaporated to provide the curde product which was purified by column chromatography [silica; CH$_3$OH/CH$_2$Cl$_2$(20:1)] to give 6.5 g (78%) of product as a syrup.

Step D:
3,4-Dihydro-4-hydroxy-2-(3-methoxy)propyl-2H-thieno[3,2-e]-1,2-thiazine-6-sulfonamide-1,1-dioxide The product from Step C (6.5 g, 18.6 mmol) was dissolved in THF (40 mL), cooled to −78° C. and treated sequentially with n-butyllithium, sulfur dioxide, and hydroxylamine-O-sulfonic acid in a manner essentially identical to that described in Example 2, Step D to provide the desired crude product which, after purification by column chromatography, provided 4.1 g (62%) of an amber syrup.

Step E:
3,4-Dihydro-2-(3-methoxy)propyl-4-oxo-2H-thieno[3,2-e]-1,2-thiazine-6-sulfonamide-1,1-dioxide To a solution of the product from Step D (3.8 g, 10.7 mmol) in acetone (40 mL) at room temperature was added Jones reagent [9.7 mL (prepared by dissolving CrO$_3$ (7 g) in H$_2$O (50 mL) and adding H$_2$SO$_4$ (6.1 mL)]. This mixture was stirred at room temperature for one hour, diluted with ethyl acetate (200 mL) and washed with a 5% solution of sodium bisulfite (2×100 mL) and brine (2×50 mL), dried (MgSO$_4$), and evaporated to a syrup which was purified by column chromatography [silica; CH$_3$OH/CH$_2$Cl$_2$(20:1)] to give 2.7 g (70%) of the desired product: mp 115°–117° C.

Step F:
(+)-3,4-Dihydro-4-hydroxy-2-(3-methoxy)propyl-2H-thieno[3,2-e]-1,2-thiazine-6-sulfonamide-1,1-dioxide To a solution of the product of Step E (2.6 g, 7.34 mmol) in THF (30 mL) at −78° C. was added a solution of (+)-β-chlorodiisopinocampheylborane (11.8 g, 36.7 mmol) in THF (10 mL). The reaction mixture was allowed to warm to −20° C. and kept at this temperature for 4 days. Diethanolamine (4.2 mL, 44 mmol) was added to the reaction mixture and the solution stirred for 30 min, diluted with EtOAc (150 mL), washed with water (2×50 mL) and brine (2×50 mL), dried (MgSO$_4$), and evaporated to a syrup which was purified by column chromatography [silica; CH$_3$OH/CH$_2$Cl$_2$(20:1)] to give 2.4 g (92%) of the desired compound as a colorless foam.

Step G:
(−)-4-Ethylamino-3,4-dihydro-2-(3-methoxy)propyl-2H-thieno[3,2-e]-1,2-thiazine-6-sulfonamide-1,1-dioxide hydrochloride To a solution of the product from Step F (2.4 g, 6.74 mmol) and triethylamine (3.8 mL, 27 mmol) in anhydrous tetrahydrofuran (20 mL) cooled to −20° C. was added tosyl chloride (2.6 g, 13.5 mmol); this mixture was allowed to warm to room temperature and stirred for 18 hr. The reaction mixture was cooled to −60° C. and ethylamine (10 mL) was added and the mixture was again allowed to warm to room temperature. After 18 hr the reaction mixture was diluted with ethyl acetate (200 mL), washed with a saturated aqueous solution of sodium bicarbonate (3×50 mL), dried (MgSO$_4$), and evaporated to give the crude product which was purified by column chromatography [silica; CH$_3$OH/CH$_2$Cl$_2$(20:1)] to give 1.3 g (52%) of the desired amine. The free base was dissolved in ethanol (5 mL) and treated with a 2M solution of hydrochloric acid in ethanol (4 mL) at room temperature. Evaporation of the solvent provided a solid which was recrystallized from methanol: methylene chloride to give 950 mg (34%) of the desired product; mp 175°–177° C.; [α]$_D$ −17.1° (C=1.00, H$_2$O). Analysis. Calculated for C$_{12}$H$_{22}$ClN$_3$O$_5$S$_3$: C, 34.32; H, 5.28; N, 10.00 Found: C, 34.26; H, 5.23; N, 9.92.

EXAMPLE 26

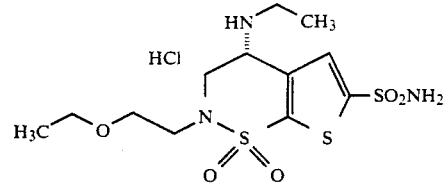

(+)-2-(2-Ethoxy)ethyl-4-ethylamino-3,4-dihydro-2H-thieno[3,2-e]-1,2-thiazine-6-sulfonamide-1,1-dioxide hydrochloride By following essentially the same procedure as used for the preparation of Example 25 but using instead 2-bromoethylethyl ether for the alkylation reaction in Step A, and omitting step C, the desired compound was prepared; mp 211°–213° C.,[α]$_D$+9.4° (C=1.00, CH$_3$OH). Analysis. Calculated for C$_{12}$H$_{22}$ClN$_3$O$_5$S$_3$: C, 34,32; H, 5.28; N, 10.00. Found: C, 34.27; H, 5.28; N, 9.92.

EXAMPLE 27

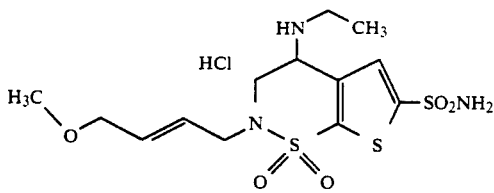

4-Ethylamino-3,4-dihydro-2-trans-(4-methoxy)-2-butenyl]-2H-thieno[3,2-e]-1,2-thiazine-6-sulfonamide-1,1-dioxide hydrochloride

Step A:
3,4-Dihydro-4-hydroxyl-2-[trans-(5-methoxy)-2-butenyl]-2H-thieno(3,2-e]-1,2-thiazine-6-sulfonamide-1,1-dioxide By following essentially the same procedure as that used for the preparation of the product of Example 25, Step D, but substituting trans-1,4-dibromo-2-butene for 1,3-dibromopropane in Step A, the desired compound was obtained as a syrup which was directly used in the subsequent reaction.

Step B:
4-Ethylamino-3,4-dihydro-2-[trans-(4-methoxy)-2-butenyl]-2H-thieno[3,2-e]-1,2-thiazine-6-sulfonamide-1,1-dioxide hydrochloride The product from Step A (2 g, 5.43 mmol) was treated sequentially with p-toluenesulfonyl chloride, ethylamine, and hydrochloric acid as described for Step G of Example 25 to give 920 mg (50%) of product as a colorless solid: mp 110°–115° C. Analysis. Calculated for $C_{13}H_{22}ClN_3O_5S_3 \cdot 0.5H_2O$: C, 35.40; H, 5.25; N, 9.52. Found: C, 35.39; H, 5.34; N, 9.27.

EXAMPLE 28

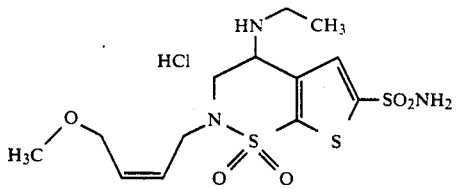

4-Ethylamino-3,4-dihydro-2-[cis-(4-methoxy)-2-butenyl]-2H-thieno[3,2-e]-1,2-thiazine-6-sulfonamide-1,1-dioxide hydrochloride By following the same procedure as that described in Example 27, but substituting cis-1,4-dichloro-2-butene for trans-1,4-dibromo-2-butene in Step A, the desired compound was obtained as a crystalline solid: mp 200°–205° C. Analysis. Calculated for $C_{13}H_{22}ClN_3O_5S_3 \cdot 0.5H_2O$: C, 35.40; H, 5.25; N, 9.52. Found: C, 35.15; H, 5.34; N, 9.36.

EXAMPLE 29

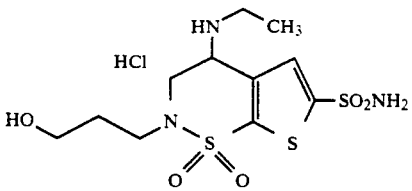

4-Ethylamino-3,4-dihydro-2-(3-hydroxy)propyl-2H-thieno[3,2-e]-1,2-thiazine-6-sulfonamide-1,1-dioxide hydrochloride

Step A:
3,4-Dihydro-4-hydroxy-2-(3-hydroxy)propyl-2H-thieno[3,2-e]-1,2-thiazine The product from Example 2, Step C (8.0 g, 30 mmol) was dissolved in anhydrous DMF (80 mL), cooled to −20° C and sodium hydride (1.1 g, 46.8 mmol) was added. After stirring for ten minutes 3-bromopropanol (5.3 mL, 58.5 mmol) was added and the reaction mixture was stirred for 24 hr at room temperature. The solvent was removed by evaporation and the residue was dissolved in ethyl acetate (300 mL). This solution was washed with brine (3 x 50 mL), dried ($MgSO_4$), and evaporated to give a crude product which was purified by column chromatography [silica; $CH_3OH/CH_2Cl_2(10:1)$] to provide 5.3 g (53%) of desired product as a syrup which was directly used in the next reaction.

Step B: 4-[(1-Ethoxy)ethoxy]-2-[3-[(1-ethoxy)ethoxy]propyl-3,4-dihydro-2H-thieno-[3,2-e]-1,2-thiazine The product from Step A (4.4 g, 16.7 mmol) and p-toluenesulfonic acid (1.6 g) were dissolved in THF (40 mL) and cooled to −10° C. at which point ethylvinyl ether (6.4 mL, 67 mmol) was added. This mixture was allowed to warm to 0° C. and kept at this temperature for 7 hr followed by dilution with cold ethyl acetate (500 mL). The organic layer was separated, washed with saturated sodium bicarbonate (2×200 mL), dried ($MgSO_4$), and evaporated to provide 6 g of crude product which was used in the next step without further purification.

Step C:
3,4-Dihydro-4-hydroxy-2-(3-hydroxy)propyl-2H-thieno[3,2-e]-1,2-thiazine-6-sulfonamide-1,1-dioxide The product from Step B (7 g, 17.2 mmol) was dissolved in THF (50 mL), cooled to −78° C. and treated sequentially with n-butyllithium, sulfur dioxide, and hydroxylamine-O-sulfonic acid in a manner essentially identical to that described in Example 2, Step E to provide the desired crude product as a syrup which, after purification by column chromatography [silica; $CH_3OH/CH_2Cl_2(10:1)$], provided 1.5 g (26%) of a colorless foam.

Step D:
2-[3-(tert-Butyldimethylsilyloxy)propyl]-3,4-dihydro-4-hydroxy-2H-thieno[3,2-e]-1,2-thiazine-6-sulfonamide-1,1-dioxide To a solution of the product from Step C (1.4 g, 4 mmol) in DMF (14 mL) at room temperature and under a blanket of nitrogen was added imidazole (300 mg, 4.4 mmol) and tert-butyldimethylsilyl chloride (904 mg, 6 mmol). The reaction mixture was stirred at room temperature for 5 hr and the solvent removed by evaporation to give a residue. The residue was dissolved in ethyl acetate (150 mL) and the solution washed with water (2×50 mL) and brine (2×50 mL), dried (MgSO4), and evaporated to a syrup which was purified by a column chromatography silica; CH3OH/CH2Cl2(10:1)] to give 1.05 g (58%) of product as an oil.

Step E:
2-[3-(tert-Butyldimethylsilyloxy)propyl]-4-ethylamino-3,4-dihydro-2H-thieno[3,2-e]-1,2-thiazine-6-sulfonamide-1,1-dioxide To a solution of the product of Step D (1.4 g , 3 mmol) and triethylamine (1.7 mL, 12 mmol) in THF (10 mL) at −20° C. was added p-toluenesulfonyl chloride (1.2 g, 6 mmol) and the reaction mixture was stirred at 0° C. for 5 hr. The reaction mixture was cooled to −78° C. at which point ethylamine (10 mL) was added; this mixture was allowed to warm to reflux temperature for 2 hr and then maintained at room temperature for 40 hr. After removing the solvent the crude product was diluted with ethyl acetate (150 mL), washed with water (2×50 mL) and brine (2×50 mL), dried (MgSO4), and evaporated to a syrup which was purified by column chromatography [silica; CH3OH/CH2Cl2(20:1)] to give 900 mg (64%) as a colorless foam.

Step F:
4-Ethylamino-2-(3-hydroxy)propyl-3,4-dihydro-2H-thieno[3,2-e]-1,2-thiazine-6-sulfonamide-1,1-dioxide hydrochloride The product from Step E (900 mg, 1.86 mmol) was dissolved in a 1M solution of tetrabutylammonium fluoride in THF (10 mL) and stirred at room temperature for 20 hr under a nitrogen atmosphere. After removal of the solvent, the residue was dissolved in ethyl acetate (100 mL) and this solution was washed with a saturated aqueous solution of sodium bicarbonate (2×50 mL), water (3×25 mL) and brine (3×25 mL), dried (MgSO4), and evaporated to a syrup which was purified by column chromatography [silica; CH3OH/CH2Cl2(10:1)] to give 600 mg (87%) of free base as a syrup. This syrup was dissolved in ethanol (3 mL), and a 2M solution of hydrochloric acid in ethanol (2 mL) was added followed by evaporation to provide a solid which was dissolved in water (5 mL) and evaporated. Recrystallization from methanol/methylene chloride gave 480 mg of the desired product: mp 203°-205° C. Analysis Calculated for C11H20ClN3O5S3: C, 32,55; H, 4.96; N, 10.35. Found C, 32.43; H, 4.92; N, 10.28.

EXAMPLE 30

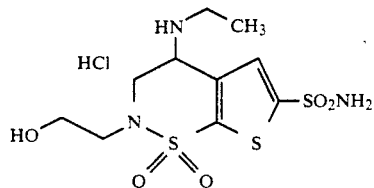

4-Ethylamino-3,4-dihydro-2-(2-hydroxy)ethyl-2H-thieno[3,2-e]-1,2-thiazine-6-sulfonamide-1,1-dioxide hydrochloride By following the same procedure as that described in Example 29, but substituting 2-bromoethanol for 3-bromopropanol in Step A, the desired compound was obtained as a crystalline solid: mp 228°-230° C. Analysis Calculated for C10H18ClN3O5S3: C, 30.65; H, 4.63; N, 10.72. Found C, 30.78; H, 4.68, N, 10.59.

EXAMPLE 31

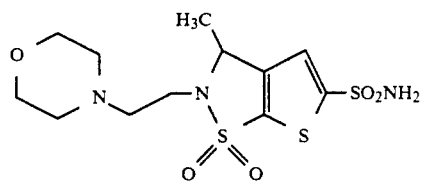

2,3-Dihydro-3-methyl-2-[2-(4-morpholinyl)ethyl]-thieno13,2-d]isothiazole-5-sulfonamide-1,1-dioxide Step A: 3-Methylthieno[3,2-d]isothiazole The product from Example 2, Step A (10.37 g, 48.8 mmol) was dissolved in anhydrous ether (100 mL), cooled to −20° C. and a 2.5M solution of n-butyllithium in hexanes (21.5 mL, 49 mmol) was slowly added. The mixture was allowed to warm to 0° C. and stirred at this temperature for two hours, again cooled to −20° C. at which point sulfur (1.56 g, 48.8 mmol) was added in small portions. The cooling bath was removed and the mixture was allowed to warm to room temperature over a two hour period followed by the addition of 2 N HCl (10 mL). The ether layer was separated, washed with brine (3×25 mL) and evaporated to a residue which was mixed with THF (100 mL) and 2N HCl (10 mL) and heated at 45° C. for 45 min followed by the addition of solid sodium bicarbonate to neutralize the mixture. The organic layer was separated, washed with brine (3×25 mL), dried (MgSO4), and evaporated to a solid which was recrystallized from methylene chloride/hexane to give 4.6 g (60%) of a solid (150°-152° C.). This solid was suspended in dioxane (400 mL), water (5 mL) was added, and the mixture degassed under nitorgen. Concentrated hydrochloric acid (1 mL) was added to this mixture followed by triphenylphosphine (18.7 g, 71.2 mmol). This mixture became homogenous after 15 min and was stirred for one additional hour, diluted with water (IL, and extracted with ether (4×100 mL). The combined extracts were washed with water (3×100 mL), brine (2×100 mL), and evaporated to a residue which was dissolved in aqueous THF (400 mL, 1:1) to which was added hydroxylamine-0-sulfonic acid (8.1 g, 71.2 mmol). This mixture was stirred for 45 min followed by the addition of sodium carbonate (18.9 g, 178 mmol) and stirring continued at room temperature for 18 hr. The reaction mixture was diluted with water (500 mL) and extracted with ether (3×150 mL). The combined extracts were dried (Na2CO3) and evaporated to a residue which was purified by column chromatography (silica, hexane/ethyl acetate) to provide 22.1 g (65%) of the desired compound as an amber oil.

Step B:
2,3-Dihydro-3-methyl-thieno[3,2-d]isothiazole-1,1-dioxide

To a solution of the product from Step A (4.23 g, 27.2 mmol) in methylene chloride (40 mL) which had been degassed under nitrogen and cooled to 0° C. was added m-chloroperbenzoic acid (5.9 g, 24.1 mmol). After stirring for six hours the reaction mixture was filtered and the solvent removed. The residue was dissolved in dry THF (50 mL), cooled in an ice bath, and NaBH$_4$ (1.7 g, 41 mmol) was added followed by allowing the reaction mixture to warm to room temperature with continued stirring for 18 hr. Water (25 mL) was added to the reaction mixture and after the pH was adjusted to 6.0 with 2N HCl it was extracted with ethyl acetate (3×10 mL). The combined extracts were dried (MgSO$_4$) and evaporated to a residue which was purified by column chromatography (silica, hexane/ethyl acetate) to provide 1.31 g (25%) of product: mp 79°–81° C.

Step C:
2,3-Dihydro-3-methyl-2-[2-(4-morpholinyl)ethyl]-thieno[3,2-d]isothiazole-1,1-dioxide The product from Step B (1.06 g, 5.62 mmol) was added to a suspension of NaH (0.97 g, 22.5 mmol) in DMF (19 mL) followed by chloroethylmorpholine hydrochloride (2.11 g, 11.21 mmol), and the mixture was warmed to 80° C. at which point NaI (1.1 g) was added and the mixture stirred for 20 min. The reaction mixture was diluted with water (80 mL) and extracted with methylene chloride (3×25 mL). The combined extracts were evaporated to a residue which was dissolved in ethyl acetate (80 mL) and the solution was extracted with 2N HCl (3×20 mL); this aqueous solution was adjusted to pH 7.5 with 2N NaOH and extracted with ethyl acetate (3×15 mL). The combined extracts were dried (MgSO$_4$) and evaporated to a residue which was purified by column chromatography [silica, CH$_2$Cl$_2$/CH$_3$OH(3:1)] to give 1.68 g (98%) of the desired product as an oil.

Step D:
2,3-Dihydro-3-methyl-2-[2-(4-morpholinyl)ethyl]-thieno[3,2-d]isothiazole-5-sulfonamide-1,1-dioxide The product from Step C (0.69 g, 2.28 mmol) was dissolved in anhydrous THF (10 mL), degassed under nitrogen and then cooled to −60° C. A solution of t-butyllithium (3.0 mL of a 1.7 M solution in pentane, 5.02 mmol) was added rapidly and the mixture was allowed to warm to 0° C.; after one hour the mixture was cooled to −10° C. and excess sulfur dioxide gas was passed into the reaction flask until the mixture was acidic. The mixture was then concentrated and the residue mixed with water (10 mL). Sodium acetate trihydrate (1.55 g, 11.4 mmol) and hydroxylamine-O-sulfonic acid (0.77 g, 6.84 mmol) were added and the mixture was stirred at ambient temperature for 18 hr. The reaction mixture was saturated with sodium chloride, and extracted with ethyl acetate (5×2 mL). The combined extracts were dried (MgSO$_4$) and evaporated to provide the desired product as a syrup.

EXAMPLE 32

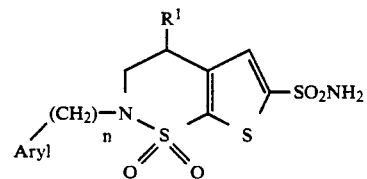

Using the procedures outlined in Examples 20 and 21, but substituting the appropriate haloalkyl-heteroaromatic or haloalkylphenyl compound in Step A or Step B, respectively, compounds such as the following can be prepared:

| R$^1$ | n | Aryl |
|---|---|---|
| NHEt | 1 | thien-2-yl |
| NHEt | 2 | thien-2-yl |
| NHEt | 1 | 5-methylthien-2-yl |
| NHEt | 1 | 5-methylthien-3-yl |
| NHEt | 1 | 1-methylpyrazol-3-yl |
| OH | 1 | imidazol-4-yl |
| OH | 1 | 1-methylimidazol-4-yl |
| OH | 2 | 1-methylimidazol-4-yl |
| NHEt | 1 | pyridazin-3-yl |
| OEt | 1 | 3-(morpholinomehtyl)phenyl |

Many of the haloalkylheteroaromatic or haloalkyl-phenyl compounds which are used as starting materials can be obtained from commercial sources. Yet other such desired starting materials can be prepared from these commercially available compounds or by other methods which are known to one skilled in the art. An important lead reference which discloses the synthesis of haloalkylheteroaromatic compounds is "Comprehensive Heterocylcic Chemistry," A. R. Katritzky et al., Volumes 2–6.

Using the procedures described in equations 1 to 7, the Examples 1 to 32 and other well known procedures one skilled in the art can prepare the compounds listed in Tables 1 to 7.

In Tables 1 to 7 the following symbols correspond to the chemical structures: Me is CH$_3$; Et is CH$_2$CH$_3$; n-Pr is CH$_2$CH$_2$CH$_3$; i-Pr is CH(CH$_3$)$_2$; i-Bu is CH$_2$CH(CH$_3$)$_2$; t-Bu is C(CH$_3$)$_3$ and Ph is C$_6$H$_5$.

TABLE 1

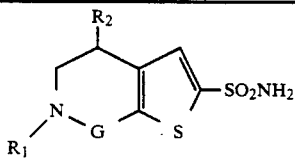

| G | R$_1$ | R$_2$ |
|---|---|---|
| SO$_2$ | H | HNMe |
| SO$_2$ | H | HNEt |
| SO$_2$ | Me | HNMe |
| SO$_2$ | Me | HNEt |
| SO$_2$ | Et | HNEt |

TABLE 1-continued

| G | R₁ | R₂ |
|---|---|---|
| $SO_2$ | n-Pr | HNEt |
| $SO_2$ | i-Pr | HNEt |
| $SO_2$ | $CH_2CHCH_2$ | HNEt |
| $SO_2$ | $CH_2CCH$ | HNEt |
| $SO_2$ | $(CH_2)_2OMe$ | HNEt |
| $SO_2$ | $(CH_2)_2OMe$ | $EtNC(=O)OEt$ |
| $SO_2$ | $(CH_2)_2OMe$ | $EtNC(=O)CH_3$ |
| $SO_2$ | $(CH_2)_2OH$ | HNEt |
| $SO_2$ | $(CH_2)_3OEt$ | HNEt |
| $SO_2$ | $(CH_2)_3OEt$ | HNn-Pr |
| $SO_2$ | $(CH_2)_3OH$ | HNEt |
| $SO_2$ | $(CH_2)_3OH$ | HNn-Pr |
| $SO_2$ | $(CH_2)_3OC(=O)CH_3$ | HNEt |
| $SO_2$ | $(CH_2)_2OMe$ | HNn-Pr |
| $SO_2$ | $(CH_2)_3OEt$ | HNEt |
| $SO_2$ | $(CH_2)_2OEt$ | HNn-Pr |
| $SO_2$ | $(CH_2)_3OMe$ | HNEt |
| $SO_2$ | $(CH_2)_3OMe$ | HNn-Pr |
| $SO_2$ | $(CH_2)_3OMe$ | HNi-Bu |
| $SO_2$ | $(CH_2)_2O(CH_2)_2OMe$ | HNEt |
| $SO_2$ | $(CH_2)_2O(CH_2)_2OMe$ | HNn-Pr |
| $SO_2$ | $(CH_2)_2O(CH_2)_2OMe$ | HNi-Bu |
| $SO_2$ | $(CH_2)_3O(CH_2)_2OMe$ | HNEt |
| $SO_2$ | $(CH_2)_3O(CH_2)_2OMe$ | HNn-Pr |
| $SO_2$ | $(CH_2)_3O(CH_2)_2OMe$ | HNi-Bu |
| $SO_2$ | $CH_2CHCHCH_2OMe$ (trans) | HNEt |
| $SO_2$ | $CH_2CHCHCH_2OMe$ (trans) | HNn-Pr |
| $SO_2$ | $CH_2CHCHCH_2OMe$ (trans) | HNi-Bu |
| $SO_2$ | $CH_2CHCHCH_2OMe$ (cis) | HNEt |
| $SO_2$ | $CH_2CHCHCH_2OMe$ (cis) | HNn-Pr |
| $SO_2$ | $CH_2CHCHCH_2OMe$ (cis) | HNi-Bu |
| $SO_2$ | Me | $HNCH_2CHCH_2$ |
| $SO_2$ | Me | $HNC_3H_5$ |
| $SO_2$ | Me | $HNCH_2C_3H_5$ |
| $SO_2$ | Me | HNn-Pr |
| $SO_2$ | Me | HNi-Bu |
| $SO_2$ | Me | $HN(CH_2)_3OH$ |
| $SO_2$ | Me | $HN(CH_2)_3OMe$ |
| $SO_2$ | Me | OH |
| $SO_2$ | Me | OMe |
| $SO_2$ | Me | Oi-Bu |
| $SO_2$ | Me | $O(CH_2)_2N(CH_2CH_2)_2O$ |
| $SO_2$ | Me | $O(CH_2)_2N(CH_2CH_2)_2NCOMe$ |
| $SO_2$ | Me | 4-Cl—Ph |
| $SO_2$ | Me | 3-N(Me)₂—Ph |
| $SO_2$ | Me | 3-$CH_2$)N($CH_2CH_2$)₂O—Ph |
| $SO_2$ | $(CH_2)_2N(CH_2CH_2)_2O$ | OMe |
| $SO_2$ | $(CH_2)_2N(CH_2CH_2)_2O$ | OH |
| $SO_2$ | $(CH_2)_2N(CH_2CH_2)_2O$ | OEt |
| $SO_2$ | $(CH_2)_2N(CH_2CH_2)_2NCOMe$ | $CH_2OMe$ |
| $SO_2$ | $(CH_2)_2N(CH_2CH_2)_2NCOMe$ | OEt |
| $SO_2$ | $(CH_2)_2N(CH_2CH_2)_2NCOMe$ | OH |
| $SO_2$ | $(CH_2)_2N(CH_2CH_2)_2O$ | CONHEt |
| $SO_2$ | $(CH_2)_5Me$ | HNEt |
| $SO_2$ | $(CH_2)_3OMe$ | HNEt |
| $SO_2$ | $CH_2CONHMe$ | HNEt |
| $SO_2$ | Ph | HNEt |
| $SO_2$ | 4-Cl—Ph | HNEt |
| $SO_2$ | 4-CONHMe—Ph | HNEt |
| $SO_2$ | 4-$SO_2NMe_2$—Ph | HNEt |
| $SO_2$ | 3-$SO_2Me$—Ph | HNEt |
| $SO_2$ | 4-$OCF_2H$—Ph | HNEt |
| $SO_2$ | 4-OMe—Ph | HNEt |
| $SO_2$ | 4-OH, 3-$CH_2NMe_2$—Ph | HNEt |
| $SO_2$ | 4-NHCOMe—Ph | HNEt |
| $SO_2$ | $CH_2$-4-pyridyl | HNEt |
| $SO_2$ | $(CH_2)_2OH$ | HNEt |
| $SO_2$ | $(CH_2)_3OEt$ | HNEt |
| $SO_2$ | $(CH_2)_2COMe$ | HNEt |
| $SO_2$ | $CH_2CON(CH_2CH_2)_2N(CH_2)_2OMe$ | OEt |
| $SO_2$ | $CH_2CO_2i$-Pr | HNEt |
| $SO_2$ | $(CH_2)_2N(CH_2CH_2)_2O$ | $OCH_2CH_2OH$ |

TABLE 1-continued

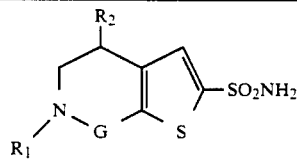

| G | $R_1$ | $R_2$ |
|---|---|---|
| CO | H | HNMe |
| CO | H | HNEt |
| CO | Me | HNn-Pr |
| CO | Me | NHi-Bu |
| CO | Me | HN(CH$_2$)$_2$OH |
| CO | Me | HN(CH$_2$)$_3$OMe |
| CO | Me | OH |
| CO | Me | OMe |
| CO | Me | Oi-Bu |
| CO | Me | O(CH$_2$)$_2$N(CH$_2$CH$_2$)$_2$O |
| CO | Me | O(CH$_2$)$_2$N(CH$_2$CH$_2$)$_2$NCOMe |
| CO | Me | 4-Cl—Ph |
| CO | Me | 3-N(Me)$_2$—Ph |
| CO | Me | 3-CH$_2$N(CH$_2$CH$_2$)$_2$O—Ph |
| CO | (CH$_2$)$_2$N(CH$_2$CH$_2$)$_2$O | OMe |
| CO | (CH$_2$)$_2$N(CH$_2$CH$_2$)$_2$O | OEt |
| CO | (CH$_2$)$_2$N(CH$_2$CH$_2$)$_2$NCOMe | CH$_2$OMe |
| CO | (CH$_2$)$_2$N(CH$_2$CH$_2$)$_2$NCOMe | OEt |
| CO | (CH$_2$)$_2$N(CH$_2$CH$_2$)$_2$O | CONHEt |
| CO | (CH$_2$)$_5$Me | HNEt |
| CO | (CH$_2$)$_2$OMe | HNEt |
| CO | CH$_2$CONHMe | HNEt |
| CO | Ph | HNEt |
| CO | 4-Cl—Ph | HNEt |
| CO | 4-CONHMe—Ph | HNEt |
| CO | 4-SO$_2$NMe$_2$—Ph | HNEt |
| CO | 3-SO$_2$Me—Ph | HNEt |
| CO | 4-OCF$_2$H—Ph | HNEt |
| CO | 4-OMe—Ph | HNEt |
| CO | 4-OH, 3-CH$_2$NMe$_2$—Ph | HNEt |
| CO | 4-NHCOMe—Ph | HNEt |
| CO | (CH$_2$)$_2$OH | HNEt |
| CO | (CH$_2$)$_2$OEt | HNEt |
| CO | (CH$_2$)$_2$COMe | HNEt |
| CO | CH$_2$CON(CH$_2$CH$_2$)$_2$N(CH$_2$)$_2$OMe | OEt |
| CO | CH$_2$CO$_2$i-Pr | HNEt |
| CO | (CH$_2$)$_2$N(CH$_2$CH$_2$)$_2$O | OCH$_2$CH$_2$OH |

TABLE 2

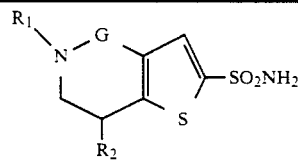

| G | $R_1$ | $R_2$ |
|---|---|---|
| SO$_2$ | H | HNMe |
| SO$_2$ | H | HNEt |
| SO$_2$ | Me | HNn-Pr |
| SO$_2$ | Me | HNi-Bu |
| SO$_2$ | Me | HN(CH$_2$)$_2$OH |
| SO$_2$ | Me | HN(CH$_2$)$_3$OMe |
| SO$_2$ | Me | OH |
| SO$_2$ | Me | OMe |
| SO$_2$ | Me | Oi-Bu |
| SO$_2$ | Me | O(CH$_2$)$_2$N(CH$_2$CH$_2$)$_2$O |
| SO$_2$ | Me | O(CH$_2$)$_2$N(CH$_2$CH$_2$)$_2$NCOMe |
| SO$_2$ | Me | 4-Cl—Ph |
| SO$_2$ | Me | 3-N—(Me)$_2$—Ph |
| SO$_2$ | Me | 3-CH$_2$N(CH$_2$CH$_2$)$_2$O—Ph |
| SO$_2$ | (CH$_2$)$_2$N(CH$_2$CH$_2$)$_2$O | OMe |
| SO$_2$ | (CH$_2$)$_2$N(CH$_2$CH$_2$)$_2$O | OEt |
| SO$_2$ | (CH$_2$)$_2$N(CH$_2$CH$_2$)$_2$NCOMe | CH$_2$OMe |
| SO$_2$ | (CH$_2$)$_2$N(CH$_2$CH$_2$)$_2$NCOMe | OEt |
| SO$_2$ | (CH$_2$)$_2$N(CH$_2$CH$_2$)$_2$O | CONHEt |
| SO$_2$ | (CH$_2$)$_5$Me | HNEt |
| SO$_2$ | (CH$_2$)$_3$OMe | HNEt |

TABLE 2-continued

| G | $R_1$ | $R_2$ |
|---|---|---|
| $SO_2$ | $(CH_2)CONHMe$ | HNEt |
| $SO_2$ | Ph | HNEt |
| $SO_2$ | 4-Cl—Ph | HNEt |
| $SO_2$ | 4-CONHMe—Ph | HNEt |
| $SO_2$ | 4-$SO_2NMe_2$—Ph | HNEt |
| $SO_2$ | 3-$SO_2Me$—Ph | HNEt |
| $SO_2$ | 4-$OCF_2H$—Ph | HNEt |
| $SO_2$ | 4-OMe—Ph | HNEt |
| $SO_2$ | 4-OH, 3-$CH_2NMe_2$—Ph | HNEt |
| $SO_2$ | 4-NHCOMe—Ph | HNEt |
| $SO_2$ | $(CH_2)_2OH$ | HNEt |
| $SO_2$ | $(CH_2)_2OEt$ | HNEt |
| $SO_2$ | $(CH_2)_2COMe$ | HNEt |
| $SO_2$ | $CH_2CON(CH_2CH_2)_2N(CH_2)_2OMe$ | OEt |
| $SO_2$ | $CH_2CO_2$i-Pr | HNEt |
| $SO_2$ | $(CH_2)_2N(CH_2CH_2)_2O$ | $OCH_2CH_2OH$ |
| CO | H | HNMe |
| CO | H | HNEt |
| CO | Me | HNn-Pr |
| CO | Me | HNi-Bu |
| CO | Me | $HN(CH_2)_2OH$ |
| CO | Me | $HN(CH_2)_3OMe$ |
| CO | Me | OH |
| CO | Me | OMe |
| CO | Me | Oi-Bu |
| CO | Me | $O(CH_2)_2N(CH_2CH_2)_2O$ |
| CO | Me | $O(CH_2)_2N(CH_2CH_2)_2NCOMe_2$ |
| CO | Me | 4-Cl—Ph |
| CO | Me | 3-$N(Me)_2$—Ph |
| CO | Me | 3-$CH_2N(CH_2CH_2)_2O$—Ph |
| CO | $(CH_2)_2N(CH_2CH_2)_2O$ | OMe |
| CO | $(CH_2)_2N(CH_2CH_2)_2O$ | OEt |
| CO | $(CH_2)_2N(CH_2CH_2)_2NCOMe$ | $CH_2OMe$ |
| CO | $(CH_2)_2N(CH_2CH_2)_2NCOMe$ | OEt |
| CO | $(CH_2)_2N(CH_2CH_2)_2O$ | CONHEt |
| CO | $(CH_2)_5Me$ | HNEt |
| CO | $(CH_2)_2OMe$ | HNEt |
| CO | $CH_2CONHMe$ | HNEt |
| CO | Ph | HNEt |
| CO | 4-Cl—Ph | HNEt |
| CO | 4-CONHMe—Ph | HNEt |
| CO | 4-$SO_2NMe_2$—Ph | HNEt |
| CO | 3-$SO_2Me$—Ph | HNEt |
| CO | 4-$OCF_2H$—Ph | HNEt |
| CO | 4-OMe—Ph | HNEt |
| CO | 4-OH, 3-$CH_2NMe_2$—Ph | HNEt |
| CO | 4-NHCOMe—Ph | HNEt |
| CO | $(CH_2)_2OH$ | HNEt |
| CO | $(CH_2)_2OEt$ | HNEt |
| CO | $(CH_2)_2COMe$ | HNEt |
| CO | $CH_2CON(CH_2CH_2)_2N(CH_2)_2OMe$ | OEt |
| CO | $CH_2CO_2$i-Pr | HNEt |
| CO | $(CH_2)_2N(CH_2CH_2)_2O$ | $OCH_2CH_2OH$ |

TABLE 3

| $R_1$ | $R_2$ | $R_3$ |
|---|---|---|
| $(CH_2)_2N(CH_2CH_2)_2O$ | H | H |
| $(CH_2)_2N(CH_2CH_2)_2O$ | H | H |
| $(CH_2)_2N(CH_2CH_2)_2O$ | Et | H |
| $(CH_2)_2N(CH_2CH_2)_2O$ | Me | H |
| $(CH_2)_2N(CH_2CH_2)_2O$ | Me | Me |
| $(CH_2)_2N(CH_2CH_2)_2O$ | H | Cl |
| $(CH_2)_2N(CH_2CH_2)_2O$ | H | Br |

TABLE 3-continued $$\text{R}_1\text{R}_2\text{N-S(O}_2\text{)-[thiophene with R}_3\text{]-SO}_2\text{NH}_2$$

| R₁/R₂ | R₃ | (third col) |
|---|---|---|
| (CH₂)₂N(CH₂CH₂)₂O | H | CH₂OEt |
| (CH₂)₂N(CH₂CH₂)₂O | H | CH₂OMe |
| (CH₂)₂N(CH₂CH₂)₂O | H | CH₂Oi-Pr |
| (CH₂)₂N(CH₂CH₂)₂O | H | CH₂Oi-Bu |
| (CH₂)₂N(CH₂CH₂)₂O | H | CH₂OH |
| (CH₂)₂N(CH₂CH₂)₂O | H | CH(CH₃)OH |
| (CH₂)₂N(CH₂CH₂)₂O | Me | CH₂CONHEt |
| (CH₂)₂N(CH₂CH₂)₂NCOMe | H | H |
| (CH₂)₂N(CH₂CH₂)₂NCOMe | H | H |
| (CH₂)₂N(CH₂CH₂)₂NCOMe | Me | H |
| (CH₂)₂N(CH₂CH₂)₂NCOMe | Me | Me |
| (CH₂)₂N(CH₂CH₂)₂NCOMe | H | Cl |
| (CH₂)₂N(CH₂CH₂)₂NCOMe | H | Br |
| (CH₂)₂N(CH₂CH₂)₂NCOMe | H | CH₂OEt |
| (CH₂)₂N(CH₂CH₂)₂NCOMe | H | CH₂OMe |
| (CH₂)₂N(CH₂CH₂)₂NCOMe | H | CH₂Oi-Pr |
| (CH₂)₂N(CH₂CH₂)₂NCOMe | H | CH₂Oi-Bu |
| (CH₂)₂N(CH₂CH₂)₂NCOMe | H | CH₂OH |
| (CH₂)₅Me | H | CH₂N(CH₂CH₂)₂O |
| (CH₂)₂OMe | H | CH₂N(CH₂CH₂)₂O |
| (CH₂)₂OH | H | CH₂N(CH₂CH₂)₂O |
| CH₂CONHMe | H | CH₂N(CH₂CH₂)₂O |
| Ph | H | CH₂N(CH₂CH₂)₂NCOMe |
| 4-Cl—Ph | H | Me |
| 4-CONHMe—Ph | H | Me |
| 4-SO₂NMe₂—Ph | H | Me |
| 3-SO₂Me—Ph | H | Me |
| 4-OCF₂H—Ph | H | Me |
| 4-OMe—Ph | Me | Me |
| 4-OH, 3-CH₂NMe₂—Ph | Me | Me |
| 4-NHCOMe—Ph | Me | Me |
| (CH₂)₂OH | Me | Me |
| (CH₂)₂OEt | Me | Me |
| (CH₂)₂COMe | Me | Me |
| CH₂CON(CH₂CH₂)₂N(CH₂)₂OMe | Me | H |
| CH₂CO₂i-Pr | Me | Me |
| (CH₂)₂N(CH₂CH₂)₂O | H | CH₂CH₂OH |
| (CH₂)₂N(CH₂CH₂)₂NCOMe | H | CH₂CH₂OH |
| Me | Me | CH₂NH(CH₂)₂OCH₃ |
| Me | Me | CH₂NH(CH₂)₃CF₃ |
| CH₂CHCH₂ | H | CH₂NH(CH₂)₂OCH₃ |

| R₁ and R₂ | R₃ |
|---|---|
| —(CH₂CH₂)₂N(CH₂)₂OMe | H |
| —(CH₂CH₂)₂N(CH₂)₂OMe | Me |
| —(CH₂CH₂)₂N(CH₂)₂OH | H |
| —(CH₂CH₂)₂N(CH₂)₂OH | Br |
| —(CH₂CH₂)₂N(CH₂)₂OMe | Cl |
| —(CH₂CH₂)₂N(CH₂)₂OMe | CH₂OH |
| —(CH₂CH₂)₂N(CH₂)₂OMe | CH₂OMe |
| —(CH₂CH₂)₂NCH₂CONHMe | H |
| —(CH₂CH₂)₂N(CH₂)₂CONHMe | H |

TABLE 4

$$\text{R}_2\text{R}_1\text{N-S(O}_2\text{)-[thiophene with R}_3\text{]-SO}_2\text{NH}_2$$

| R₁ | R₂ | R₃ |
|---|---|---|
| (CH₂)₂N(CH₂CH₂)₂O | H | H |
| (CH₂)₂N(CH₂CH₂)₂O | H | H |
| (CH₂)₂N(CH₂CH₂)₂O | Me | H |
| (CH₂)₂N(CH₂CH₂)₂O | Me | Me |
| (CH₂)₂N(CH₂CH₂)₂O | H | Cl |
| (CH₂)₂N(CH₂CH₂)₂O | H | Br |
| (CH₂)₂N(CH₂CH₂)₂O | H | CH₂OEt |
| (CH₂)₂N(CH₂CH₂)₂O | H | CH₂OMe |
| (CH₂)₂N(CH₂CH₂)₂O | H | CH₂Oi-Pr |
| (CH₂)₂N(CH₂CH₂)₂O | H | CH₂Oi-Bu |
| (CH₂)₂N(CH₂CH₂)₂O | H | CH₂OH |
| (CH₂)₂N(CH₂CH₂)₂O | H | CH(CH₃)OH |

TABLE 4-continued

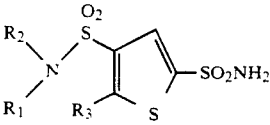

| R₁ | R₃ | (R₂ is H unless noted) |
|---|---|---|
| (CH₂)₂N(CH₂CH₂)₂O | Me | CH₂CONHEt |
| (CH₂)₂N(CH₂CH₂)₂NCOMe | H | H |
| (CH₂)₂N(CH₂CH₂)₂NCOMe | Me | H |
| (CH₂)₂N(CH₂CH₂)₂NCOMe | Me | Me |
| (CH₂)₂N(CH₂CH₂)₂NCOMe | H | Cl |
| (CH₂)₂N(CH₂CH₂)₂NCOMe | H | Br |
| (CH₂)₂N(CH₂CH₂)₂NCOMe | H | CH₂OEt |
| (CH₂)₂N(CH₂CH₂)₂NCOMe | H | CH₂OMe |
| (CH₂)₂N(CH₂CH₂)₂NCOMe | H | CH₂Oi-Pr |
| (CH₂)₂N(CH₂CH₂)₂NCOMe | H | CH₂Oi-Bu |
| (CH₂)₂N(CH₂CH₂)₂NCOMe | H | CH₂OH |
| (CH₂)₅Me | H | CH₂N(CH₂CH₂)₂O |
| (CH₂)₂OMe | H | CH₂N(CH₂CH₂)₂O |
| (CH₂)₂OH | H | CH₂N(CH₂CH₂)₂O |
| (CH₂CONHMe | H | CH₂N(CH₂CH₂)₂O |
| Ph | H | CH₂N(CH₂CH₂)₂NCOMe |
| 4-Cl—Ph | H | Me |
| 4-CONHMe—Ph | H | Me |
| 4-SO₂NMe₂—Ph | H | Me |
| 3-SO₂Me—Ph | H | Me |
| 4-OCF₂H—Ph | H | Me |
| 4-OMe—Ph | Me | Me |
| 4-OH, 3-CH₂NMe₂—Ph | Me | Me |
| 4-NHCOMe—Ph | Me | Me |
| (CH₂)₂OH | Me | Me |
| (CH₂)₂OEt | Me | Me |
| CH₂CON(CH₂CH₂)₂N(CH₂)₂OMe | Me | H |
| CH₂CO₂i-Pr | Me | Me |
| (CH₂)₂N(CH₂CH₂)₂O | H | CH₂CH₂OH |
| (CH₂)₂N(CH₂CH₂)₂NCOMe | H | CH₂CH₂OH |

| R₁ and R₂ | R₃ |
|---|---|
| —(CH₂CH₂)₂N(CH₂)₂OMe | H |
| —(CH₂CH₂)₂N(CH₂)₂OMe | Me |
| —(CH₂CH₂)₂N(CH₂)₂OMe | Cl |
| —(CH₂CH₂)₂N(CH₂)₂OMe | CH₂OH |
| —(CH₂CH₂)₂N(CH₂)₂OMe | CH₂OMe |
| —(CH₂CH₂)₂NCH₂CONHMe | H |
| —(CH₂CH₂)₂N(CH₂)₂CONHMe | H |

TABLE 5

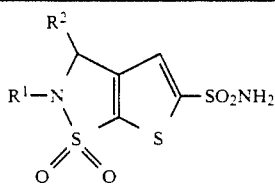

| R¹ | R² |
|---|---|
| Me | CH₂NHMe |
| Me | CH₂NHEt |
| Et | CH₂NHEt |
| n-Pr | CH₂NHEt |
| Et | CH₂NHMe |
| n-Pr | CH₂NHMe |
| CH₂CH=CH₂ | CH₂NHMe |
| Me | CH₂NHCH₂CH₂OCH₃ |
| Et | CH₂NHCH₂CH₂OCH₃ |
| n-Pr | CH₂NHCH₂CH₂OCH₃ |
| Et | CH₂NHCH₂CH₂OH |
| CH₂CH₂OCH₃ | CH₂NHMe |
| CH₂CH₂OCH₃ | CH₂NHEt |
| CH₂CH₂CH₂OH | CH₂NHMe |
| CH₂CH₂CH₂OH | CH₂NHEt |
| CH₂CH₂CH₂OCH₃ | CH₂NHEt |
| C₆H₅ | CH₂NHCH₂CH₂OH |
| C₆H₅ | CH₂NHCH₂CH₂OCH₃ |
| C₆H₄(3-SO₂CH₃) | CH₂NHEt |
| C₆H₄(3-OH) | CH₂NHEt |
| C₆H₄[3-SO₂N(CH₃)₂] | CH₂NHEt |

TABLE 5-continued

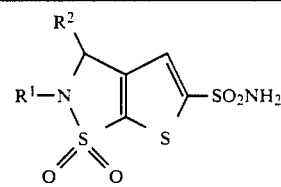

| R¹ | R² |
|---|---|
| CH₂C₆H₅ | CH₂NHEt |
| 2-thenyl | CH₂NHEt |
| 2-thenyl(5-SO₂CH₃) | CH₂NHEt |
| CH₂CH₂N(CH₂CH₂)₂O | H |
| CH₂CH₂N(CH₂CH₂)₂O | CH₃ |
| CH₂CH₂N(CH₂CH₂)₂O | CH₂OH |
| CH₂CH₂N(CH₂CH₂)₂O | CH₂OCH₃ |
| CH₂CH₂N(CH₂CH₂)₂O | CH₂CH₂OH |
| CH₂CH₂N(CH₂CH₂)₂O | CH₂OCH₂CH₂OH |
| CH₂CH₂N(CH₂CH₂OH)₂ | CH₃ |
| CH₂CH₂N(CH₂CH₂OCH₃)₂ | CH₃ |
| CH₂CH₂N(CH₃)CH₂CH₂OCH₃ | CH₃ |
| CH₂CH₂N(CH₂CH₂)₂NCOCH₃ | H |
| CH₂CH₂N(CH₂CH₂)₂NCOCH₃ | CH₃ |
| CH₂CH₂N(CH₂CH₂)₂NCOCH₃ | CH₂OH |
| CH₂CH₂N(CH₂CH₂)₂NCOCH₃ | CH₂CH₂OH |
| CH₂CH₂NHCH₂CH₂F | CH₃ |
| CH₂CH₂NHCH₂CH₂F | CH₂CH₂OH |
| CH₂CH₂N(CH₂CH₂)₂NCHO | H |
| CH₂CH₂N(CH₂CH₂)₂NCHO | CH₃ |
| CH₂CH₂N(CH₂CH₂)₂NCH₂CH₂OCH₃ | H |

TABLE 5-continued $$R^1-N\begin{array}{c}R^2\\|\\\end{array}\underset{S}{\overset{S}{\diagdown}}SO_2NH_2$$

(with SO₂ bridge)

| $R^1$ | $R^2$ |
|---|---|
| $CH_2CH_2N(CH_2CH_2)_2NCH_2CH_2OCH_3$ | $CH_3$ |
| $CH_2CH_2N(CH_2CH_2)_2NCH_2CH_2OCH_3$ | $CH_2OCH_3$ |
| $CH_2CH_2(imidazo-2-yl)$ | H |
| $CH_2CH_2(imidazo-2-yl)$ | $CH_3$ |
| $CH_2CH_2(imidazo-2-yl)$ | $CH_2OCH_3$ |
| $CH_2$-4-pyridinyl | $CH_2OCH_3$ |
| $C_6H_4(3-CH_2NH(CH_2)_2OCH_3$ | H |
| $C_6H_4(4-CH_2NH(CH_2)_2OCH_3$ | H |
| $C_6H_4[3-CH_2N(CH_2CH_2)_2O]$ | H |
| $C_6H_3(3-CH_2NHMe_2)(4-OH)$ | $CH_3$ |
| $C_6H_3(3-CH_2NHMe_2)(4-OMe)$ | $CH_2OCH_3$ |

TABLE 6

$$R^4\diagdown\underset{R^1}{\overset{R^3}{\diagdown}}\underset{N}{\overset{R^2}{\diagup}}\underset{S}{\overset{}{\diagdown}}SO_2NH_2$$

| $R^1$ | $R^2$ | $R^3$ | $R^4$ |
|---|---|---|---|
| $CH_3$ | NHEt | H | H |
| $CH_2CH_3$ | NHEt | H | H |
| $CH_2CH_2OCH_3$ | NHEt | H | H |
| $CH_2CH_2OH$ | NHEt | H | H |
| $CH_3$ | H | NHEt | H |
| $CH_3$ | H | H | $CH_2OH$ |
| $CH_2CH_2N(CH_2CH_2)_2O$ | H | H | H |

TABLE 7

$$R_3\diagdown\underset{R_1}{\overset{R_2}{\diagdown}}\underset{N}{\overset{}{\diagup}}\underset{S}{\overset{}{\diagdown}}SO_2NH_2$$

| $R^1$ | $R^2$ | $R^3$ |
|---|---|---|
| $CH_3$ | HNEt | $CH_3$ |
| $(CH_2)_3OCH_3$ | HNEt | $CH_3$ |
| $CH_3$ | H | $CH_2NHEt$ |
| $CH_3$ | H | $CH_2NH(CH_2)_2OCH_3$ |
| $CH_3$ | H | $CH_2N(CH_2)_2O$ |
| $CH_3$ | H | $3-CH_2NH(CH_2)_2OCH_3Ph$ |
| $CH_3$ | H | $CH_3$ |

The following examples are representative ophthalmic formulations including the thiophene sulfonamides of the present invention. The formulations can be administered topically to the eye 1 to 3 drops 1 to 4 times per day according to the discretion of a skilled clinician.

EXAMPLE 32

Ophthalmic Suspension

| Ingredient | Concentration (wt %) |
|---|---|
| Dihydro-4-methoxy-2-methyl-2H-thieno[3,2-3]-1,2-thiazine-6-sulfonamide-1,1-dioxide (Compound) | 3.0% |
| Hydroxypropylmethylcellulose | 0.5% |
| Dibasic Sodium Phosphate | 0.2% |
| Disodium Edetate | 0.01% |
| Sodium Chloride | 0.8% |
| Purified Water | q.s. |
| Benzalkonium Chloride | 0.01% |
| Polysorbate 80 | 0.1% |
| NaOH/HCl | pH 7.02 |

The Compound (0.09 g), benzalkonium chloride (0.03 g), polysorbate 80 (0.15 g) can be mixed together in water (1.23 g) and ball milled for approximately 4 h. A hydroxypropylmethyulcelluslose vehicle can be prepared by mixing 2% aqueous hydroxypropylmethylcellulose (40 g), sodium chloride (1.28 g), dibasic sodium phosphate (0.32 g), disodium edetate (0.016 g), sodium chloride (1.28 g) and water (35 g) together and the pH adjusted to 7.4 by the addition of 1N HCl (250 μL). A portion of this vehicle (1.5 mL) can be added to the mixture containing the Compound to furnish the desired suspension.

EXAMPLE 33

Ophthalmic Solution

| Ingredient | Concentration (wt %) |
|---|---|
| 3,4-Dihydro-4-ethylamino-2-methyl-2H-thieno[3,2-e]-1,2-thiazine-6-sulfonamide-1,1-dioxide hydrochloride (Compound) | 2.0% |
| Hydroxyethylcellulose | 0.5% |
| Monobasic Sodium Phosphate | 0.13% |
| Dibasic Sodium Phosphate | 0.01% |
| Benzalkonium Chloride | 0.01% |
| Disodium Edetate | 0.01% |
| Purified Water | q.s. |
| NaCl (Osmalality = 282 mOsm) | 0.4% |
| HCl/NaOH | pH 5.0 |

The Compound (0.06 g) and sodium chloride (0.014 g) were mixed together in water (1.44 g) and the pH of the solution was adjusted to 5.02 by the addition of 1N NaOH (10 μL). The hydroxyethylcellulose vehicle was prepared by mixing together monobasic sodium phosphate (0.26 g), dibasic sodium phosphate (0.02 g) and disodium edetate (0.02) in water (96.7 g). The benzalkonium chloride (2.0 g) and hydroxyethylcellulose were added to the mixture and the pH was adjusted to 5.01 by the addition of 1N HCl (100 μl). A portion of this vehicle (1.5 g) was added to the solution containing the compound and the pH was adjusted to 5.03 by the addition of 1N NaOH (10 μL).

EXAMPLE 34

Ophthalmic Gel

| Ingredient | Concentration (wt %) |
|---|---|
| 3,4-Dihydro-2-methyl-4-(2-methyl)propyl-amino-2H-thieno[3,2-e]-1,2-thiazine-6-sulfonamide-1,1-dioxide hydrochloride (Compound) | 0.1% |
| Mannitol | 3.6% |

-continued

| Ingredient | Concentration (wt %) |
| --- | --- |
| Benzalkonium Chloride | 0.01% |
| Carbopol | 3.0% |
| HCl/NaOH | pH 5.0 |
| Purified Water | q.s. |

The mannitol (0.18 g), benzalkonium chloride (0.05 mL), Compound (0.1 g) and carbopol (0.15 g) can all be added to water (4.3 mL) and mixed well. The pH can be adjusted to pH 5.0 and purified water (q.s. to 5 mL) can be added and mixed well to form a gel.

EXAMPLE 35

Ophthalmic Solution

| Ingredient | Concentration (wt %) |
| --- | --- |
| R-(+)-4-Ethylamino-3,4-dihydro-2-methyl-2H-thieno[3,2-e]-1,2-thiazine-6-sulfonamide 1,1-dioxide hydrochloride (Compound) | 2.27% |
| Hydroxypropylmethylcellulose | 3.3% |
| Sodium Acetate Dihydrate | 0.1% |
| Mannitol (Osmolality - 282 mOsm) | 2.44% |
| Benzalkonium Chloride | 0.01% |
| Disodium Edetate | 0.01% |
| Purified Water | q.s. |
| HCl/NaOH | pH 5.0 |

The sodium acetate (0.2 g). disodium edta (0.02 g), benzylalkonium chloride (2.1 g of a 1% solution) and mannitol (5.32 g) were dissolved in water for injection (115 mL). The pH was adjusted to 5.0 with 1N sodium hydroxide and the final volume was adjusted to 117 mL with water for injection. Hydroxypropylmethylcellulose (83.0 g of an 8% solution) was mixed with the 117 mL of the acetate buffer solution to furnish the vehicle. To prepare the final formulation, 0.068 g of the Compound was diluted with vehicle to make 3.0 mL total volume and the pH was adjusted to 5.0 with 1N sodium hydroxide (5 μL).

EXAMPLE 36

Ophthalmic Solution

| Ingredient | Concentration (wt %) |
| --- | --- |
| R-)+)4-Ethylamino-3,4-dihydro-2-(2-methoxy)ethyl-2H-thieno[3,2-e]-1,2-thiazine-6-sulfonamide-1,1-dioxide hydrochloride (Compound) | 1.69% |
| Hydroxypropylmethylcellulose | 3.0% |
| Sodium Acetate trihydrate | 0.1% |
| Mannitol (Osmolality = 317 mOsm) | 2.4% |
| Benzalkonium Chloride | 0.01% |
| Disodium Edetate | 0.01% |
| Purified Water | q.s. |
| HCl/NaOH | pH 6.4 |

The above ingredients were mixed together in substantially the same manner as described in Example 35 to furnish the ophthalmic solution.

EXAMPLE 37

Ophthalmic Solution

| Ingredient | Concentration (wt %) |
| --- | --- |
| R-(+)-3,4-Dihydro-2-(2-methoxy)ethyl-4-propylamino-2H-thieno[3,2-e]-1,2-thiazine-6-sulfonamide-1,1-dioxide hydrochloride (Compound) | 2.19% |
| Hydroxypropylmethylcellulose | 3.0% |
| Sodium Acetate trihydrate | 0.1% |
| Mannitol (Osmolality = 288 mOsm) | 2.4% |
| Benzalkonium Chloride | 0.01% |
| Disodium Edetate | 0.01% |
| Purified Water | q.s |
| HCl/NaOH | pH 0.5 |

The above ingredients were mixed together in substantially the same manner as described in Example 35 to furnish the ophthalmic solution.

EXAMPLE 38

Ophthalmic Suspension

| Ingredient | Concentration (wt %) |
| --- | --- |
| (−)4-Ethylamino-3,4-dihydro-2-(3-methoxy)propyl-2H-thieno[3,2-e]-1,2-thiazine-6-sulfonamide-1,1-dioxide hydrochloride (Compound) | 2.0% |
| Hydroxypropylmethylcellulose | 0.5% |
| Dibasic Sodium Phosphate | 0.2% |
| Disodium Edetate | 0.01% |
| Sodium Chloride | 0.8% |
| Purified Water | q.s. |
| Benzalkonium Chloride | 0.01% |
| Polysorbate 80 | 0.1% |
| NaOH/HCl | pH 7.1 |

The above ingredients can be mixed together in substantially the same manner as described in Example 32 to furnish the ophthalmic suspension.

We claim:

1. A compound selected from the group consisting of:
   3,4-Dihydro-2-(2-methoxy)ethyl-4-propylamino-2H-thieno[3,2-e]-1,2-thiazine-6-sulfonamide 1,1-dioxide;
   2-(2-Ethoxyethyl-)-4-ethylamino-3,4-dihydro-2H-thieno[3,2-e]-1,2-thiazine-6-sulfonamide 1,1-dioxide;
   2-(2-Ethoxy)ethyl-3,4-dihydro-4-propylamino-2H-thieno[3,2-e]-1,2-thiazine-6-sulfonamide 1,1-dioxide;
   4-Ethylamino-3,4-dihydro-2-(3-methoxy)propyl-2H-thieno[3,2-e]-1,2-thiazine-6-sulfonamide 1,1-dioxide;
   3,4-Dihydro-2-(3-methoxy)propyl-4-propylamino-2H-thieno[3,2-e]-1,2-thiazine-6-sulfonamide 1,1-dioxide;
   3,4-Dihydro-2-[2-(methoxyethoxy)ethyl]-4-propylamino-2H-thieno[3,2-e]-1,2-thiazine-6-syulfonamide 1,1-dioxide;
   4 Ethylamino-3,4-dihydro-2-[2-(methoxyethoxy)ethyl]-2H-thieno[3,2-e]-1,2-thiazine-6-sulfonamide 1,1-dioxide;
   4-Ethylamino-3,4-dihydro-2-[3-(methoxyethoxy)-propyl]-2H-thieno[3,2-e]-1,2-thiazine-6-sulfonamide 1,1-dioxide; and
   3,4-Dihydro-2-[3-(methoxyethoxy)propyl]-4-propylamino-2H-thieno[3,2-e]-1,2-thiazine-6-sulfonamide 1,1-dioxide.

2. The compound of claim 10 which is 3,4-Dihydro-2-(2-methoxy)ethyl-4-propylamino-2H-thieno[3,2-e]-1,2-thiazine-6-sulfonamide 1,1-dioxide.

3. The Compound of claim 1 which is 4-Ethylamino-3,4-dihydro-2-(3-methoxy)propyl-2H-thieno[3,2-e]-1,2-thiazine-6-sulfonamide -1,1-dioxide.

4. R-(+)-4-Ethylamino-3,4-dihydro-2-(2-methoxy)ethyl-2H-thieno[3,2-e]-1,2-thiazine-6-sulfonamide 1,1-dioxide.

5. R-(+)-3,4-Dihydro-2-(2-methoxy)ethyl-4-propylamino-2H-thieno[3,2-e]-1,2-thiazine-6-sulfonamide 1,1-dioxide.

6. A formulation for controlling intraocular pressure comprising a therapeutically effective amount of the compound of claim 1 in a pharmaceutically acceptable carrier.

7. The formulation of claim 6 wherein the compound concentration is between about 0.1 and 10% by weight.

8. A formulation for controlling intraocular pressure comprising a therapeutically effective amount of the compound of claim 4 in a pharmaceutically acceptable carrier.

9. The formulation of claim 8 wherein the compound concentration is between about 0.1 and 10% by weight.

10. The formulation of claim 9 wherein the concentration is between about 0.25 wt % and 5.0 wt %.

11. A formulation for controlling intraocular pressure comprising a therapeutically effective amount of the Compound of claim 5 in a pharmaceutically acceptable carrier.

12. The formulation of claim 11 wherein the compound concentration is between about 0.1 and 10% by weight.

13. The formulation of claim 12 wherein the concentration is between about 0.25 wt % and 5.0 wt %.

14. A method for controlling intraocular pressure which comprises topically administering to the affected eye a therapeutically effective amount of the compound of claim 1.

* * * * *

UNITED STATES PATENT AND TRADEMARK OFFICE
CERTIFICATE OF CORRECTION

PATENT NO. : 5,240,923

DATED : Aug. 31, 1993

INVENTOR(S) : Dean et al.

It is certified that error appears in the above-identified patent and that said Letters Patent is hereby corrected as shown below:

Column 9, line 35, change

" " to -- --

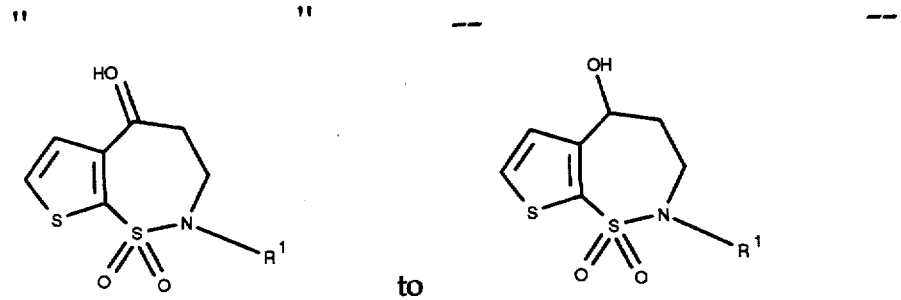

Column 9, line 40, change

" " to -- --

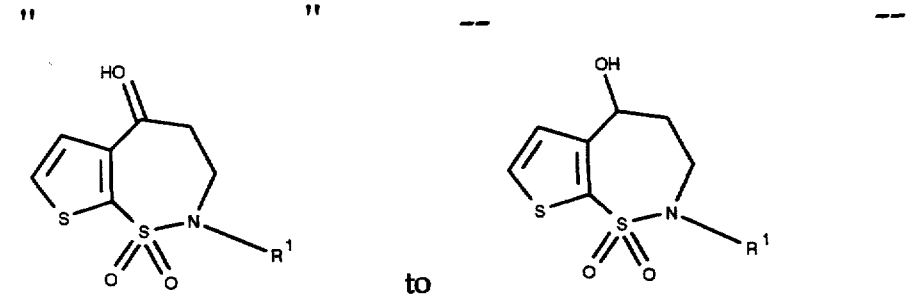

UNITED STATES PATENT AND TRADEMARK OFFICE
CERTIFICATE OF CORRECTION

PATENT NO. : 5,240,923

DATED : Aug. 31, 1993

INVENTOR(S) : Dean et al.

It is certified that error appears in the above-identified patent and that said Letters Patent is hereby corrected as shown below:

Column 16, lines 63-64, change "2,3-dihydro-4-hydroxy-2H-thieno [2,3-e]-1,2-thiazine 1,1-dioxide" to --3,4-dihydro-4-hydroxy-2H-thieno[3,2-e]-1,2-thiazine 1,1-dioxide--.

Column 17, line 55, change "3,4-Dihydro-4-hydroxy-2-12-(4-morpholinyl)" to --3,4-Dihydro-4-hydroxy-2-[2-(4-morpholinyl)--.

Column 17, lines 62-63, change 2,3-dihydro-4-hydroxy-2H-thieno [2,3-e]-1,2-thiazine" to --3,4-dihydro-4-hydroxy-2H-thieno[3,2-e]-1,2-thiazine--.

Column 27, line 44, change "3,4-Dihydro-2-(2-methoxy)ethyl-4-oxo-2H" to --2,3-Dihydro-2-(2-methoxy)ethyl-4-oxo-4H--.

Column 29, line 24, change "thieno3,2-e]" to --thieno[3,2-e]--.

Column 29, line 33, change "1-dioxide" to --1,1-dioxide--.

Column 29, line 51, change "thieno 3,2-e]" to --thieno [3,2-e]--.

Column 30, line 4, change "thieno3,2-e]-1,2-thiazine ],1-dioxide" to --thieno[3,2-e]-1,2-thiazine 1,1-dioxide--.

UNITED STATES PATENT AND TRADEMARK OFFICE
CERTIFICATE OF CORRECTION

PATENT NO. : 5,240,923
DATED : Aug. 31, 1993
INVENTOR(S) : Dean et al.

It is certified that error appears in the above-identified patent and that said Letters Patent is hereby corrected as shown below:

Column 30, line 23, change "thieno3,2-e]" to --thieno[3,2-e]--.

Column 32, line 41, change "3,4-Dihydro-hydroxy" to --3,4-Dihydro-4-hydroxy--.

Column 33, line 14, change "hydroxy-2-2-imidazol-1-yl)ethyl" to --hydroxy-2-[2-imidazol-1-yl)ethyl]--.

Column 33, line 55, change "dihydro-2-2-(4-morpholinyl)ethyl]" to --dihydro-2-[2-(4-morpholinyl)ethyl]--.

Column 35, line 44, change "3,4-Dihydro-2-(3-methoxy)propyl-4-oxo-2H-thieno" to 2,3-Dihydro-2-(3-methoxy)propyl-4-oxo-4H-thieno--.

Column 40, line 24, change "thieno13,2-d]isothiazole" to --thieno[3,2-d]isothiazole--.

Column 54, line 7, change "[3,2-3]-1,2-thiazine" to --3,4-Dihydro[3,2-e]-1,2-thiazine--.

Column 56, line 65, change "claim 10" to --claim 1--.

Signed and Sealed this

Seventeenth Day of January, 1995

Attest:

BRUCE LEHMAN

*Attesting Officer*     *Commissioner of Patents and Trademarks*